(12) United States Patent
Yang et al.

(10) Patent No.: US 8,512,757 B2
(45) Date of Patent: Aug. 20, 2013

(54) MICELLES FOR DRUG DELIVERY

(75) Inventors: Yi-Yan Yang, Singapore (SG);
Shao-Qiong Liu, Singapore (SG)

(73) Assignee: Agency for Science, Techology and Research, Singapore (SG)

(*) Notice: Subject to any disclaimer, the term of this patent is extended or adjusted under 35 U.S.C. 154(b) by 629 days.

(21) Appl. No.: 12/307,356

(22) PCT Filed: Jul. 5, 2006

(86) PCT No.: PCT/SG2006/000188
§ 371 (c)(1),
(2), (4) Date: Jun. 22, 2009

(87) PCT Pub. No.: WO2008/004978
PCT Pub. Date: Jan. 10, 2008

(65) Prior Publication Data
US 2010/0159019 A1    Jun. 24, 2010

(51) Int. Cl.
*A61K 9/14* (2006.01)
*A61K 47/32* (2006.01)
*A61K 47/34* (2006.01)
*C08G 81/02* (2006.01)

(52) U.S. Cl.
USPC ............... 424/497; 424/78.17; 424/78.31; 424/78.37; 514/772.1; 514/772.4; 514/772.3; 514/77.6; 525/54.1; 525/54.21; 525/191; 523/201

(58) Field of Classification Search
USPC ..... 424/497, 78.17, 78.31, 78.37; 514/772.1, 514/772.4, 772.3, 772.6; 525/54.1, 54.21; 525/191; 523/201
See application file for complete search history.

(56) References Cited

U.S. PATENT DOCUMENTS

2005/0118252 A1  6/2005  Bae et al.
2005/0277739 A1  12/2005  Yang et al.

OTHER PUBLICATIONS

Chung et al., "Thermo-responsive drug delivery from polymeric micelles constructed using block copolymers of poly(N-isopropylacrylamide) and poly(butylmethacrylate)," 1999, Journal of Controlled Release, 62, 115-127.
Drummond et al., "Current status of pH-sensitive liposomes in drug delivery," 2000, Progress in Lipid Research, 39, 409-460.
Kohori et al., "Control of adriamycin cytotoxic activity using thermally responsive polymeric micelles composed of poly(N-isopropylacrylamide-co-N, N-dimethylacrylamide)-b-poly(D,L-lactide)," 1999, Colloids and Surfaces B. Biointerfaces, 16, 195-205.
Lee et al., "Poly(L-histidine)-PEG block copolymer micelles and pH-induced destabilization," 2003, Journal of Controlled Release, 90, 363-374.
Lee et al., "Polymeric micelled for tumor pH and folate-mediated targeting," 2003, Journal of Controlled Release, 91, 103-113.
PubMed Online Abstracts, PMID 15970560, Wei et al., "Temperature- and pH-sensitive core-shell nanoparticles self-assembled from poly(n-isopropylacrylamide-co-acrylic acid-co-cholesteryl acrylate) for intracellular delivery of anticancer drugs," 2005, Front. Biosci., (10), 3058-3067.
Soppimath et al., "pH-Triggered Thermally Responsive Polymer Core-Shell Nanoparticeles for Drug Delivery," 2005, Advanced Materials, vol. 17, No. 3, 318-323.
Vaupel et al., "Heterogeneous Oxygen Partial Pressure and pH Distribution in C3H Mouse Mammary Adenocarcinoma," 1981, Cancer Research, 41, 2008-2013.
Wei et al., "Temperature- and pH-sensitive core-shell nanoparticles self-assembled from poly(n-isopropylacrylamide-co-acrylic acid-co-cholesteryl acrylate) for intracellular delivery of anticancer drugs," 2005, Frontiers in Biosciences, 10, 3058-3067.

*Primary Examiner* — Jeffrey Mullis
(74) *Attorney, Agent, or Firm* — Kilpatrick Townsend & Stockton LLP

(57) ABSTRACT

The invention provides a block copolymer comprising at least a first block and a second block. The first block comprises a plurality of temperature-sensitive monomeric units, a plurality of hydrophilic monomeric units and a plurality of targeting monomeric units, and the second block comprises a plurality of hydrophobic monomeric units. The second block comprises at least one pH-sensitive moiety.

20 Claims, 5 Drawing Sheets

MICELLES FOR DRUG DELIVERY

This application is a U.S. National Phase and claims the benefit of PCT Patent Application No. PCT/SG2006/000188, filed Jul. 5, 2006, the disclosure of which is incorporated herein by reference.

TECHNICAL FIELD

The present invention relates to a polymer for making micelles for drug delivery, and to micelles made from the polymer.

BACKGROUND OF THE INVENTION

Many anticancer drugs are taken up non-specifically by all types of cells, resulting in serious side-effects. Therefore, an ideal delivery carrier for an anticancer drug should be able to transport the drug specifically to cancer cells and release the drug molecules inside the cells to the site of their pharmacological activities. Polymer micelles have emerged recently as promising colloidal carriers for targeting poorly water-soluble and amphiphilic drugs as well as genes to tumour tissues. Using these micelles, drug targeting to solid cancers can be achieved passively through an enhanced permeability and retention effect because of their hyperpermeable angiogenic vasculature. Drug targeting can also be achieved by using a polymer sensitive to the surrounding temperature or pH. Moreover, active drug targeting can be realized by attaching biological signals, including antibodies, hormones, peptides and small compounds such as folic acid, which can recognize cancer cells, to the surface of nanoparticles. Compared to antibodies, hormones and peptides, folic acid is less expensive, more easily conjugated to nanoparticles, and more stable during transportation, storage and use. Unlike the other ligands listed, folate is nonimmunogenic, since folate is naturally found in the body. More importantly, folate receptor is frequently expressed on the surface of many human cancer cell types and cell uptake of folate-drug conjugates or folate-conjugated nano-carriers is based on folate receptor-mediated endocytosis. A similar strategy may be envisaged for targeting drug containing micelles to other diseased cells within the body.

Polymeric core-shell nanoparticles, whose shells are constructed from temperature-sensitive poly(N-isopropylacrylamide) (PNIPAAm) or its copolymers, have been well-studied. For example, doxorubicin (DOX)-incorporated micelles made from PNIPAAm-b-poly(butylmethacrylate) and PNIPAAm-b-poly(D,L-lactide) block copolymers have been reported. The core-shell nanoparticles were formed below the LCST (lower critical solution temperature) and drug release was slow. However, the micellar structure deformed at temperatures higher than the LCST, inducing DOX release. In addition, DOX release was regulated using temperature cycles through the LCST. It is expected that using thermally responsive core-shell nanoparticles, temporal drug delivery can be achieved by local heating and cooling. However such a system suffers from the disadvantage of not being easily accessible to deep tissues or tumours. An alternative approach to target drugs to tumour tissues is to use pH-sensitive carriers. The extracellular pH of most solid tumours in patients ranges from 5.7 to 7.8. The pH of the tumour interstitial fluid rarely declines below pH 6.5 and it is challenging to develop a system with such a narrow window of pH change. Recently core-shell nanoparticles made from poly(L-histidine)-b-poly(ethylene glycol) (PEG) were reported to be pH-sensitive. These nanoparticles were dissociated, thus releasing the enclosed drug, DOX, at pH from 7.4 to 6.8. However, micelles (core-shell nanoparticles) based on poly(L-histidine)-b-PEG are not stable at pH 7.4 and must mixed with poly(L-lactide)-b-PEG micelles to improve their stability. Also, the phase change in response to the external pH change was not as sharp as that induced by the temperature change.

U.S. patent application Ser. No. 10/865,681 reported pH-triggered thermally responsive core-shell nanoparticles self-assembled from the amphiphilic tercopolymer poly(N-isopropylacrylamide-co-N,N-dimethylacrylamide-co-10-undecenoic acid) [P(NIPAAm-co-DMAAm-co-UA)]. These micelles changed phase (from water-soluble, well dispersed in aqueous solution to water-insoluble, precipitated from aqueous solution) rapidly in response to an external pH change. These nanoparticles exhibited a pH-dependent lower critical solution temperature (LCST). In a normal physiological environment (pH 7.4), the LCST of the nanoparticles was well above the normal body temperature (37° C.) and the nanoparticles were thus well dispersed. In an acidic environment (i.e. tumour tissues, endosomes or lysosomes), however, the LCST was below 37° C., leading to the deformation and precipitation of the core-shell nanoparticles and to the eventual release of enclosed drug molecules. This application disclosed pH-triggered temperature-sensitive micelles made from a random copolymer of NIPAAm (temperature-sensitive), DMAAm (hydrophilic-to adjust the LCST of the polymer) and UA (a hydrophobic and pH-sensitive compound). These micelles possessed pH-dependent LCST, being higher than the normal body temperature under a simulated physiological condition (PBS, pH7.4) but lower than the normal body temperature at pH 6.6 or below. Therefore, the micelles were stable in a physiological environment but deformed and precipitated at pH 6.6 or below, releasing the enclosed drug molecules. These micelles may provide a good carrier for delivering anticancer drugs to tumour tissues (slightly acidic) or for intracellular drug delivery (escaping from the endosomes-a low pH environment and thus entering the cytosols). However, the polymer described in this application was a random amphiphilic copolymer, from which the micelles formed had a flexible core and a wide particle size distribution.

EP00822217 disclosed a diblock copolymer based on poly(ethylene oxide)-b-polyester, more specifically poly(ethylene oxide)-b-polylactide or polylactone. EP00844269 disclosed a diblock copolymer based on poly(ethylene oxide)-b-polyester or poly(methacrylic acid). The polymers claimed were similar to those disclosed in EP00822217. EP00852243 disclosed a diblock copolymer based on poly(ethylene oxide)-b-polyester or poly(methacrylic acid). On the end of poly(ethylene oxide) block, there was a sugar group. The polymers claimed were similar to those disclosed in EP00822217. All of the disclosed polymers were synthesized by ionic living polymerization, and none had pH- and temperature-sensitive functionalities.

US622903 disclosed a polymer-lipid conjugate. The hydrophilic polymer chains were releasably attached to liposomes via a disulfide bond, pH sensitive bond, enzymatically cleavable bond, or photochemically cleavable bond. After the release of the hydrophilic polymer chains, the hydrophobic segments of the liposomes were exposed to physiological membranes, providing the chance to fuse with the cell or liposome membrane.

US22082198 disclosed macromolecular micelles made from poly(ethylene glycol)-b-poly(amino acids). The amino acids carry amine groups or carboxyl groups, rendering the polymers chargeable for DNA or protein delivery. In particular, poly(ethylene glycol)-b-poly(lysine) and poly(ethylene glycol)-b-poly(aspartic acid) were disclosed. US22172711 disclosed a polymer-lipid conjugate, similar to that of US6224903.

US24077540 disclosed a pharmaceutical composition comprising a biologically active agent and a mucosal delivery-enhancing effective amount of a permeabilizing peptide. It was claimed that this pharmaceutical composition could be administered in combination with a membrane penetration-enhancing agent such as surfactant, mixed micelle and liposome. However, the types of micelles to be used were not disclosed.

WO00226241 disclosed lipid-comprising drug delivery complexes for gene delivery. The complexes comprised poly (ethylene glycol), lipid (e.g. DOTAP, DOPE, DOPC, DSPE, DLPE etc.), polycation (i.e. PEI) and targetable peptides.

WO04002404 disclosed pH-sensitive block copolymers for drug targeting to tumours. The block copolymers were made from poly(L-histidine), poly(ethylene glycol), poly(L-lactic acid) and/or poly(lactic acid-co-glycolic acid). However, the polymers contained no targeting component for targeting the copolymers to the tumours. US25025821 disclosed similar polymers to those of WO04002404. In particular, mixed micelles containing poly(L-histidine)-poly(ethylene glycol) block copolymer and poly(L-lactic acid)-poly (ethylene glycol) block copolymer were disclosed.

OBJECT OF THE INVENTION

It is an object of the present invention to overcome or substantially ameliorate at least one of the above disadvantages.

DESCRIPTION OF THE INVENTION

In a first aspect of the invention there is provided a block copolymer comprising at least a first block and a second block, wherein the first block comprises a plurality of temperature-sensitive monomeric units, a plurality of hydrophilic monomeric units and a plurality of targeting monomeric units, and the second block comprises a plurality of hydrophobic monomeric units, said second block comprising at least one pH-sensitive moiety.

Each of the hydrophobic monomeric units may comprise at least one pH-sensitive moiety, or one or more may comprise at least one pH-sensitive moiety and others may contain no pH-sensitive moiety. Each of the temperature-sensitive monomeric units may be the same as the other temperature-sensitive monomeric units, or some may be the same and some may be different. Each of the hydrophilic monomeric units may be the same as the other hydrophilic monomeric units, or some may be the same and some may be different. Each of the targeting monomeric units may be the same as the other targeting monomeric units, or some may be the same and some may be different. Each of the hydrophobic monomeric units may be the same as the other hydrophobic is monomeric units, or some may be the same and some may be different. The block copolymer may be capable of adopting a conformation in which the copolymer is in the form of a core-shell structure having a hydrophobic core and a hydrophilic shell wherein at least some of the targeting monomeric units are located in the hydrophilic shell. The block copolymer may have one of each block, or may have more than one of either the first block, the second block, or of both the first and second blocks. The block copolymer may be an AB block copolymer.

The pH-sensitive moiety may be an acidic moiety or a basic moiety. It may be for example a carboxylic acid, a sulfonic acid, a sulfinic acid, a phosphonic acid, a phosphinic acid, a thiocarboxylic acid, a dithiocarboxylic acid or some other acidic moiety, or it may be an optionally substituted amine. The pH sensitive moiety may be a moiety capable of causing the block copolymer to change conformation in response to a change in pH of a medium in which the block copolymer is located. The hydrophobic monomeric units may be derived from a polymerisable unsaturated fatty acid, e.g. a terminally unsaturated (omega-1 unsaturated) fatty acid. The fatty acid may comprise between about 2 and about 50 or more main chain carbon atoms, or between about 2 and 20, 2 and 10, 2 and 5, 5 and 50, 5 and 30, 5 and 20, 5 and 10, 10 and 50, 20 and 50, 10 and 40, 10 and 30 or 10 and 20, for example about 2, 3, 4, 5, 6, 7, 8, 9, 10, 11, 12, 14, 16, 18, 20, 22, 24, 26, 28, 30, 35, 40, 45 or 50 main chain carbon atoms. It may comprise one carbon-carbon double bond (monounsaturated), or may comprise at least 2, e.g. 2, 3 or more than 3 carbon-carbon double bonds (polyunsaturated). It may be an omega-1 fatty acid. The fatty acid may be for example (E)-9-octadecenoic acid, (Z)-9-octadecenoic acid, (Z)-11-octadecenoic acid, (E)-9-hexadecenoic acid, (Z)-9-hexadecenoic acid, (Z)-9-tetradecenoic acid, (Z)-11-ecosenoic acid, (Z)-13-docosenoic acid, (Z)-15-tetracosaenoic acid, 4-pentenoic acid, 7-octenoic acid, 10-undecenoic acid, 15-hexadecenoic acid, 19-ecosenoic acid, (E,E)-9,12-octadecadienoic acid, (Z,Z)-9,12-octadecadienoic acid, (E,E)-9,11-octadecadienoic acid, (Z,Z,Z)-9,12,15-octadecatrienoic acid, (Z,Z,Z)-6,9,12-octadecatrienoic acid, (Z,Z,Z,Z)-6,9,12,15-Octadecatetraenoic Acid, (Z,Z,)-11,14-Ecosadienoic acid, (Z,Z,Z)-5,8,11-eicosatrienoic acid, (Z,Z,Z)-11,14,17-eicosatrienoic acid, (Z,Z,Z)-8,11,14-eicosatrienoic acid, (Z,Z,Z,Z)-8,11,14,17-eicosatetraenoic acid, (Z,Z,Z,Z)-5,8,11,14-eicosatetraenoic acid, (Z,Z,Z,Z,Z)-5,8,11,14,17-eicosapentaenoic acid, (Z,Z)-13,16-docosadienoic acid, (Z,Z,Z)-13,16,19-docosatrienoic acid, (Z,Z,Z,Z)-7, 10-13-16-ocosatetraenoic acid, (Z,Z,Z,Z,Z)-4,7,10,13,16-docosapentaenoic acid, (Z,Z,Z,Z,Z)-7,10,13,16,19-docosapentaenoic acid, (Z,Z,Z,Z,Z,Z)-4,7,10,13,16,19-docosahexaenoic acid, or (Z,Z,Z,Z,Z,Z)-6,9,12,15,18,21-tetracosahexaenoic acid, or a mixture of any two or more of these. It may be straight chain or branched. It may or may not comprise cyclic structures.

The temperature sensitive monomeric unit may be capable of changing its hydrophilicity in is response to a change in temperature. The temperature sensitive monomeric unit may be capable of imparting to the block copolymer a conformation that varies with temperature. It may be capable of imparting to the block copolymer hydrophilicity that varies with temperature. It may be a monomeric unit that is capable of dehydrating (i.e. losing one or more waters of hydration) in response to an increase in temperature. The temperature sensitive monomeric unit may be derived from, for example, N-acryloylpiperidine, N-acryloylpyrrolidone, N-hydroxypropyl acrylate, hydroxymethylcellulose, N-t-butylacrylamide, N-piperidylmethacrylamide, N,N-diethylacrylamide, N-isopropylacrylamide, N-methacryloylpiperidine, N-methacryloylpyrrolidone, N-hydroxypropyl methacrylate, hydroxyethylcellulose, N-t-butylmethacrylamide, N,N-diethylmethacrylamide or N-isopropylmethacrylamide. The hydrophilic monomeric unit may comprise an amide, a carboxylic acid, a carboxylate, an amine, a hydroxylamine, a glycol or an alcohol. It may for example be derived from a member of the group consisting of acrylic acid, acrylamide, acrylate, pyrrolidone, ethylene glycol, 2-aminoethylmethacrylate and substituted derivatives thereof. The acrylamide or substituted derivative thereof may be selected from the group consisting of acrylamide (AAm), N,N'-dimethylacrylamide (DMAAm), and N-(hydroxymethyl)acrylamide.

The targeting monomeric unit may be a tumour targeting monomeric unit. The targeting monomeric unit may comprise a targeting group. It may comprise a tumour targeting group, and/or may comprise a targeting group adapted to target other specific cells (e.g. diseased cells) within the body. The targeting group may be a small molecule derived group such as folate or galactose, a peptide (e.g. an LHRH: luteinizing hormone-releasing hormone, or RGD: arginine-glycine-aspartate containing peptide), an antibody (e.g. humanised anti-CD22 antibody for targeting B cells expressing antigen CD22) or some other targeting group. The peptide may be linear or cyclic or branched. As used herein, the term "antibody" includes antibody fragments, including but not limited to, heavy chains, light chains, variable regions, constant regions, Fab, Fc, Fc receptors, single chain (scFV) antibodies, complementarity determining regions (CDRs) and any protein, polypeptide or peptide comprising an antibody, or part thereof. The targeting group may be capable of binding to a tumour, e.g. to a tumour cell, or to some other specific cells (e.g. diseased cells) within the body. The targeting monomeric unit may be derived by reaction of a targeting compound, e.g. folic acid, or a derivative thereof, with a substrate monomeric unit, whereby the substrate monomeric unit comprises a functional group capable of reacting with the targeting compound or derivative thereof in order to conjugate the targeting compound or derivative thereof to the substrate monomeric unit. The functional group may be an amine, e.g. a primary amine, or a hydroxyl group or a carboxylic acid group. Thus the targeting monomeric unit may comprise a targeting compound conjugated to a substrate monomeric unit. The substrate monomeric unit may comprise an amine group or a hydroxyl group or carboxylic acid group. It may for example be derived from aminoethyl methacrylate, aminoethyl acrylate, aminophenyl acrylate or some other suitable aminofunctional monomeric unit, acrylic acid, N-(hydroxymethyl)acrylamide or 2-hydroxyethyl methacrylate.

The first block may comprise a random copolymer block or a block copolymer block (e.g. a di-, tri-, tetra- or penta-block copolymer block) or an alternating copolymer block or some other type of copolymer block. The molecular weight of the block copolymer may be less than about 40,000, or less than about 35,000, 30,000, 25,000, 20,000, 15,000 or 10,000, or between about 2000 and about 40000, or between about 2000 and 20000, 2000 and 15000, 2000 and 1000, 5000 and 40000, 10000 and 40000, 20000 and 40000, 3000 and 20000, 3000 and 2000, 5000 and 10000 or 5000 and 8000, for example about 2000, 2500, 3000, 3500, 4000, 4500, 5000, 5500, 6000, 6500, 7000, 7500, 7600, 7700, 7800, 7900, 8000, 8500, 9000, 9500, 1000, 11000, 12000, 13000, 14000, 15000, 20000, 25000, 30000, 35000 or 40000. The molecular weight of the first block may be less than about 40,000, or less than about 35,000, 30,000, 25,000, 20,000, 15,000 or 10,000, or between about 2000 and about 40000, or between about 2000 and 20000, 2000 and 15000, 2000 and 1000, 5000 and 40000, 10000 and 40000, 20000 and 40000, 3000 and 20000, 3000 and 2000, 5000 and 10000 or 3000 and 8000, for example about 2000, 2500, 3000, 3500, 3600, 3700, 3800, 3900, 4000, 4100, 4200, 4300, 4400, 4500, 5000, 5500, 6000, 6500, 7000, 7500, 7600, 7700, 7800, 7900, 8000, 8500, 9000, 9500, 1000, 11000, 12000, 13000, 14000, 15000, 20000, 25000, 30000, 35000 or 40000. The molecular weight of the second block may be between about 200 and 2000, or between about 200 and 1500, 200 and 1000, 400 and 2000, 500 and 2000, 1000 and 2000 or 500 and 1000, for example about 200, 300, 400, 500, 600, 700, 800, 900, 1000, 1100, 1200, 1300, 1400, 1500, 1600, 1700, 1800, 1900 or 2000. It may therefore considered to be an oligomeric block. The polydispersity of each block may, independently, be narrow or broad. It may be between about 1.1 and about 3, or between about 1.1 and 2, 1.1 and 1.5, 1.3 and 3, 1.5 and 3, 2 and 3 or 1.5 and 2, and may be for example about 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3. The molecular weights may be number average, weight average, viscosity average or Z-average molecular weights. The molecular weights may be molecular weights determined by using polystyrene standards. They may be polystyrene-equivalent molecular weights.

The lower critical solution temperature (LCST) of the copolymer may be sufficiently low that the block copolymer is capable of delivering a drug associated with the hydrophobic block thereof to a tumour or other specific cells at the pH at or near the tumour or other specific cells or to endosomes (pH about 5-6.5) or lysosomes (pH about 4-5.5). The lower critical solution temperature (LCST) of the copolymer may be lower than about 37° C. at a pH of less than about 7. It may be lower than about 36.5, 36, 35.5, 35, 34, 33, 32, 31, 30, 29, 28, 27, 26, 25, 24, 23, 22, 21 or 20° C., or between about 37 and about 20° C., or between about 37 and 25, 37 and 30, 37 and 35, 37 and 36, 36 and 35, 36 and 30, 35 and 30, 36.5 and 35.5, 36.5 and 36, 35 and 20, 30 and 20, 35 and 30, 35 and 32 or 30 and 20° C., e.g. about 20, 21, 22, 23, 24, 25, 26, 27, 28, 29, 30, 31, 32, 33, 34, 35, 35.5, 35.6, 35.7, 35.8, 35.9, 36, 36.1, 36.2, 36.3, 36.4, 36.5, 36.6, 36.7, 36.8, 36.9 or 37° C. at a pH of less than about 7, or less than about 6.9, 6.8, 6.7, 6.6, 6.5, 6.4, 6.3, 6.2, 6.1, 6, 5.5 or 5, or between about 7 and about 1, 6.9 and 1, 6.8 and 1, 6.7 and 1, 6.6 and 1, 6.5 and 1, 6.4 and 1, 6.3 and 1, 6.2 and 1, 6 and 1, 5.5 and 1, 5 and 1, 4 and 1, 3 and 1, 2 and 1, 6.8 and 3, 6.8 and 5, 6.8 and 6, 6.6 and 3, 6.6 and 5 or 6.6 and 6 e.g. at about 1, 2, 3, 4, 5, 5.5, 6, 6.1, 6.2, 6.3, 6.4, 6.5, 6.6, 6.7, 6.8, 6.9 or 7. The lower critical solution temperature of the copolymer may be higher than about 37° C. at a pH of 7.4 (normal physiological pH). It may be higher than about 37.5, 38, 38.5, 39, 39.5, 40, 45 or 50° C., or may be between about 37 and about 50° C., or between about 37 and 40, 37 and 39, 37.5 and 38.5, 40 and 50, or 38 and 39° C. at normal physiological pH, and may be about 37, 37.5, 38, 38.5, 39, 39.5, 40, 41, 42, 43, 44, 45, 46, 46, 48, 49 or 50° C. at normal physiological pH.

If the number of temperature-sensitive monomeric units per molecule is m, the number of hydrophilic monomeric units per molecule is n, the number of targeting monomeric units per molecule is x, and the number of hydrophobic monomeric units per molecule is y then the following ratios may apply in the block copolymer:

m/n is between about 1 and about 100, or between about 1 and 50, 1 and 20, 1 and 10, 1 and 5, 5 and 100, 20 and 100, 50 and 100, 70 and 100, 5 and 50, 10 and 50, 20 and 50, 10 and 80, and 70, 30 and 60, 10 and 20, 20 and 30, 30 and 40, 40 and 50, 50 and 60, 60 and 70, 70 and 80, 80 and 90 or 90 and 100, e.g. about 1, 2, 3, 4, 5, 6, 7, 8, 9, 10, 15, 20, 25, 30, 35, 40, 45, 50, 55, 60, 65, 70, 75, 80, 85, 90, 95 or 100;

(m+n)/x is between about 500 and about 1, or between about 100 and 500, 100 and 400, 200 and 400, 200 and 300, or 230 and 270, e.g. about 1, 10, 100, 150, 160, 170, 180, 190, 200, 205, 210, 215, 220, 225, 230, 235, 240, 245, 250, 255, 260, 265, 270, 275, 280, 285, 290, 295, 300, 310, 320, 330, 340, 350, 400 or 500;

(m+n+x)/y is between about 2 and about 500, or between about 2 and 400, 2 and 300, 2 and 200, 2 and 100, 2 and 50, 2 and 20, 2 and 10, 10 and 500, 50 and 500, 100 and 500, 200 and 500, 300 and 500, 300 and 400, 50 and 200, 50 and 100, 100 and 400, 100 and 200 or 450 and 500, for example about 500, 470, 450, 425, 400, 375, 370, 350, 300, 250, 200, 150, 135, 120, 110, 100, 90, 80, 70, 60, 50, 40, 30, 20, 10, 9, 8, 7, 6, 5, 4, 3 or 2.

In an embodiment the ratio m:n:x:y is about 49.0:152: 0.236:3-10.

In another embodiment there is provided a block copolymer comprising at least a first block and a second block, wherein the first block comprises a plurality of temperature-sensitive monomeric units, a plurality of hydrophilic monomeric units and a plurality of targeting monomeric units, and the second block comprises a plurality of hydrophobic monomeric units, said second block comprising at least one pH-sensitive moiety or a functional group that is capable of being converted into a pH sensitive moiety and wherein each targeting monomeric unit is derived by reaction of a targeting compound or a derivative thereof with substrate monomeric unit, wherein the substrate monomeric unit comprises a functional group capable of reacting with the targeting compound or derivative thereof in order to conjugate the targeting compound or derivative thereof to the substrate monomeric unit. The functional group that is capable of being converted into a pH sensitive moiety may be a functional group capable of being converted into a carboxylic acid group or into some other acidic group, or into an amine. The functional group that is capable of being converted into a pH sensitive moiety may be for example 2-hydroxyethyl methacrylate (HEMA).

In another embodiment there is provided a block copolymer comprising at least a first block and a second block, wherein the first block comprises a plurality of temperature-sensitive monomeric units, a plurality of hydrophilic monomeric units and a plurality of targeting monomeric units, and the second block comprises a plurality of hydrophobic monomeric units, said second block comprising at least one pH-sensitive moiety, and wherein each targeting monomeric unit comprises folic acid conjugated to a substrate monomer unit.

In another embodiment there is provided a block copolymer comprising at least a first block and a second block, wherein the first block comprises a plurality of temperature-sensitive monomeric units derived from N-isopropylacrylamide, a plurality of hydrophilic monomeric units derived from N,N-dimethylacrylamide and a plurality of targeting monomeric units, and the second block comprises a plurality of hydrophobic monomeric units comprising at least one pH-sensitive moiety, wherein each hydrophobic monomeric unit is derived from a polymerisable unsaturated fatty acid and wherein each targeting monomeric unit comprises folic acid conjugated to a substrate monomer unit derived from 2-aminoethylmethacrylate.

The block copolymer may be in the form of micelles or nanoparticles. The micelles or nanoparticles may comprise a hydrophobic core and a hydrophilic shell. The block copolymer may adopt a conformation in which it comprises a hydrophobic core and a hydrophilic shell. The hydrophilic shell may comprise targeting groups. It may adopt that conformation when in a polar solvent, e.g. an aqueous solvent. The micelles or nanoparticles may have a mean diameter of between about 10 and about 400 nm, or between about 10 and 300, 10 and 200, 10 and 150, 10 and 100, 10 and 80, 10 and 50, 10 and 20, 50 and 400, 100 and 400, 200 and 400, 50 and 200, 50 and 100, 100 and 300, 100 and 200, 80 and 100, 90 and 100, 90 and 95, 95 and 100, 80 and 150, 80 and 130 or 80 and 120, e.g. about 10, 15, 20, 25, 30, 35, 40, 45, 50, 55, 60, 65, 70, 75, 80, 85, 90, 91, 92, 93, 94, 95, 96, 97, 98, 99, 100, 105, 110, 120, 130, 140, 150, 200, 250, 300, 350 or 400 nm. The size distribution may be narrow or broad. The polydispersity may be between about 0.1 and 0.5, or between about 0.1 and 0.4, 0.1 and 0.3, 0.1 and 0.2, 0.2 and 0.5, 0.3 and 0.5, 0.2 and 0.4 or 0.2 and 0.3, e.g. about 0.1, 0.15, 0.2, 0.25, 0.3, 0.35, 0.4, 0.45 or 0.5. Polydispersity P is given by:

$P = s/R$, where $s^2$ is the variance of the distribution and R is the mean particle radius. P is normally between 0 and 1.

The critical association concentration of the micelles or nanoparticles in water may be between about 5 and 200 mg/L, or between about 10 and 200, 20 and 200, 30 and 200, 50 and 200, 100 and 200, 5 and 150, 5 and 100, 5 and 50, 5 and 20, 5 and 10, 10 and 100, 10 and 50, 20 and 50, 30 and 50, 10 and 20 or 15 and 20 mg/L, e.g. about 5, 6, 7, 8, 9, 10, 11, 12, 13, 14, 15, 16, 17, 18, 19, 20, 21, 22, 23, 24, 25, 30, 35, 40, 45, 50, 60, 70, 80, 90, 100, 150 or 200 mg/L.

The invention also provides micelles or nanoparticles comprising a block copolymer according to the first aspect.

In a second aspect of the invention there is provided a process for making a block copolymer comprising:

providing a first macromonomer, said first macromonomer comprising a plurality of temperature-sensitive monomeric units, a plurality of hydrophilic monomeric units and a plurality of targeting monomeric units, and reacting the first macromonomer with a second macromonomer, said second macromonomer comprising a plurality of hydrophobic monomeric units, and said hydrophobic block comprising at least one pH-sensitive moiety or at least one group which is capable of being converted into a pH-sensitive moiety.

The step of reacting the first macromonomer with a second macromonomer may comprise copolymerising the first macromonomer with the second macromonomer, or it may comprise forming a 1:1 adduct of the first macromonomer and the second macromonomer or a 1:2 adduct or a 2:1 adduct or it may comprise some other form of reacting. The temperature sensitive monomeric units, hydrophilic monomeric units, targeting monomeric units and hydrophobic monomeric units may be as described in the first aspect. The step of providing the first macromonomer may comprise reacting a precursor macromonomer with a targeting compound, e.g. folic acid, or a derivative (e.g. an N-hydroxysuccinimide ester) thereof. The reacting may conjugate the targeting compound to the precursor macromonomer. The precursor macromonomer may comprise a plurality of temperature-sensitive monomeric units, a plurality of hydrophilic monomeric units and a plurality of substrate monomeric units, whereby each substrate monomeric unit comprises a functional group capable of reacting with the targeting compound or derivative thereof in order to conjugate the targeting compound or derivative thereof to the precursor macromonomer. The first macromonomer and/or the precursor macromonomer may comprise at least one carboxyl, hydroxyl or amino terminal group per molecule, and may comprise one terminal carboxyl, hydroxyl or amino group per molecule. The carboxyl group/ hydroxyl group/amino group may be derived from a chain transfer agent used in forming the first macromonomer and/or the precursor macromonomer. The main chain of the first macromonomer may have one or more end groups capable of reacting with, or capable of being activated so as to be capable of reacting with, an end group of the main chain of the second macromonomer. The main chain of the second macromonomer may have one or more end groups capable of reacting with, or capable of being activated so as to be capable of reacting with, an end group of the main chain of the first macromonomer.

A macromonomer in the context of this specification is a monomer (i.e. a polymerisable species) that is oligomeric or polymeric. The molecular weight of the first macromonomer (and, independently, of the precursor macromonomer) may be less than about 40,000, or less than about 35,000, 30,000, 25,000, 20,000, 15,000 or 10,000, or between about 2000 and about 40000, or between about 2000 and 20000, 2000 and 15000, 2000 and 1000, 5000 and 40000, 10000 and 40000, 20000 and 40000, 3000 and 20000, 3000 and 2000, 5000 and 10000 or 3000 and 8000, for example about 2000, 2500, 3000, 3500, 3600, 3700, 3800, 3900, 4000, 4100, 4200, 4300, 4400, 4500, 5000, 5500, 6000, 6500, 7000, 7100, 7200, 7300, 7400, 7500, 7600, 7700, 7800, 7900, 8000, 8500, 9000, 9500, 1000, 11000, 12000, 13000, 14000, 15000, 20000, 25000, 30000, 35000 or 40000. The molecular weight of the second macromonomer may be between about 200 and 2000, or between about 200 and 1500, 200 and 1000, 400 and 2000, 500 and 2000, 1000 and 2000 or 500 and 1000, for example about 200, 300, 400, 500, 600, 700, 800, 900, 1000, 1100, 1200, 1300, 1400, 1500, 1600, 1700, 1800, 1900 or 2000. It may therefore be considered to be an oligomer. The polydispersity of each macromonomer may, independently, be narrow or broad. It may be between about 1.1 and about 3, or between about 1.1 and 2, 1.1 and 1.5, 1.3 and 3, 1.5 and 3, 2 and 3 or 1.5 and 2, and may be for example about 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3.

The step of providing the first macromonomer may comprise the step of providing the precursor macromonomer. The step of providing the precursor macromonomer may comprise copolymerising a temperature-sensitive monomer, a hydrophilic monomer and a substrate monomer (or alternatively a targeting monomer derived from conjugating a targeting molecule with a substrate monomer), whereby the substrate monomer comprises a functional group capable of reacting with the targeting compound or derivative thereof following said copolymerising in order to conjugate the targeting compound or derivative thereof to the precursor macromonomer. The step of providing the precursor macromonomer may comprise a free radical copolymerisation. It may use a free radical initiator, for example benzoyl peroxide, optionally in the presence of a chain transfer agent. The chain transfer agent may be a thiol. It may be a carboxyfunctional chain transfer agent, or may be a hydroxyfunctional or aminofunctional chain transfer agent, or may comprise a functional group capable of being converted into a carboxylic acid, an amino or a hydroxyl group. It may be for example a carboxyfunctional thiol such as mercaptopropionic acid, mercaptosuccinic acid or thioglycolic add. It may be for example a hydroxyfunctional thiol such as mercaptoethanol or a thiol functional secondary alcohol. It may be an aminofunctional thiol such as 2-aminoethanethiol. The reaction may be conducted in a solvent, e.g. THF or some other suitable solvent. It may be conducted substantially in the absence of oxygen. It may be conducted under an inert atmosphere, e.g. nitrogen, carbon dioxide, helium or argon. It may be conducted at a temperature and for a time sufficient for the initiator to decompose thermally to a degree sufficient for polymerisation of the monomers. The temperature may be for example the refluxing temperature (boiling point) of the solvent. Suitable temperatures may be between about 60 and about 140° C., or between about 60 and 100, 100 and 140, 60 and 80, 80 and 100, 100 and 120 or 80 and 90° C., e.g. about 60, 70, 80, 85, 90, 100, 110, 120, 130 or 140° C. The reaction may be conducted for between about 1 and about 48 hours, or 1 and 40, 1 and 30, 1 and 20, 1 and 10, 5 and 48, 5 and 40, 5 and 30, 5 and 20, 10 and 40, 10 and 20 or 5 and 10 hours, e.g. about 1, 2, 3, 4, 5, 6, 7, 8, 9, 10, 11, 12, 13, 14, 15, 16, 17, 18, 19, 20, 24, 30, 36, 40, 44 or 48 hours. The molecular weight of the precursor macromonomer may be less than about 40,000, or less than about 35,000, 30,000, 25,000, 20,000, 15,000 or 10,000, or between about 2000 and about 40000, or between about 2000 and 20000, 2000 and 15000, 2000 and 1000, 5000 and 40000, 10000 and 40000, 20000 and 40000, 3000 and 20000, 3000 and 2000, 5000 and 10000 or 3000 and 8000, for example about 2000, 2500, 3000, 3500, 3600, 3700, 3800, 3900, 4000, 4100, 4200, 4300, 4400, 4500, 5000, 5500, 6000, 6500, 6600, 6700, 6800, 6900, 7000, 7500, 7600, 7700, 7800, 7900, 8000, 8500, 9000, 9500, 1000, 11000, 12000, 13000, 14000, 15000, 20000, 25000, 30000, 35000 or 40000.

The process may comprise activating the targeting compound, e.g. forming a derivative of the targeting compound suitable for conjugating with the substrate monomer or with one or more substrate monomeric units of a precursor macromonomer. The process may for example comprise reacting a carboxylic acid group of the targeting compound with N-hydroxysuccinimide to form an N-hydroxysuccinimide derivative (e.g. ester) of the targeting compound. The reaction may be activated using an activator such as N,N-dicyclohexylcarbodiimide (DCC). The reaction of the activated derivative with the substrate monomer or with a substrate monomeric unit within a precursor macromonomer may be conducted in a suitable solvent such as DMSO or another dipolar aprotic solvent capable of dissolving all of the reagents.

The second macromonomer comprises hydrophobic monomer units comprising at least one pH-sensitive moiety or comprising at least one group which is capable of being converted into a pH-sensitive moiety. It may be a homopolymer. It may comprise one or more carboxylic acid units as a pH-sensitive moiety. It may be a polymeric carboxylic acid. It may comprise at least one (e.g. one) terminal amino, hydroxyl or carboxyl group. The process may also comprise the step of making the second macromonomer. The step of making the second macromonomer may comprise polymerising a polymerisable hydrophobic monomer comprising at least one pH-sensitive moiety (e.g. a polymerisable carboxylic acid) or comprising a functional group that is capable of being converted into a pH sensitive moiety such as a carboxylic acid group. The polymerisable hydrophobic monomer may comprise a polymerisable double bond e.g. C=C double bond, optionally a terminal C=C double bond. The polymerisation may be a free radical polymerisation and may use a free radical initiator. It may use for example persulfate (e.g. ammonium persulfate) and may be conducted in the presence of a chain transfer agent. The chain transfer agent may be a thiol. It may comprise an amine, a hydroxyl or a carboxylic acid group. It may comprise a functional group capable of reacting with a terminal group of the first macromonomer. It may be an aminothiol, for example 2-aminoethanethiol. It may be for example a carboxyfunctional thiol such as mercaptopropionic acid, mercaptosuccinic acid or thioglycolic acid. It may be a hydroxyfunctional thiol such as mercaptoethanol or a thiol functional secondary alcohol. The chain transfer agent may be capable of forming a redox couple with the free radical initiator. In one example the polymerization is initiated by thiol radicals, generated from the reaction of aminoethanethiol hydrochloride with persulfate, according to the following equation:

$$2RSH + S_2O_8^{2-} \rightarrow 2RS + 2HSO_4^-$$

where R represents an aminoethyl group. The reaction may be conducted at neutral or alkaline pH, e.g. about 7, 7.5, 8, 8.5, 9, 9.5, 10, 10.5 or 11 or between about 7 and 11, 7 and 9, 8 and 11, 9 and 11, 8 and 10, 7.5 and 9 or 8 and 9 or 7.5 and 8.5.

In the event that the second macromonomer has a terminal carboxyl group (for example derived from a carboxyl functional chain transfer agent), it is preferable that the second macromonomer, and the hydrophobic monomer from which it is made, do not comprise a carboxyl group as a pH sensitive moiety. If it is desired that the second block of the block copolymer which is made using the second macromonomer have a carboxyl group as a pH sensitive moiety, it is preferred that the second macromonomer (and the hydrophobic monomer from which it is made) have a functional group that is capable of being converted into a carboxylic acid group, e.g. that they have a protected carboxylic acid group. The functional group that is capable of being converted into a carboxylic acid group may be for example a hydroxyl or aldehyde group (which may be oxidised to form a carboxyl group) or a carboxylic ester (e.g. trimethylsilyl, methyl, ethyl; which may be hydrolysed to form a carboxyl group) or an anhydride (e.g. acetate, sulfate, phosphate carbonate; which may be hydrolysed to form a carboxyl group). In this case, once the second macromonomer has been incorporated into a block copolymer by reaction with the first macromonomer, the functional group that is capable of being converted into a carboxylic acid group may by converted into a carboxylic acid so that the second block of the block copolymer comprises a carboxyl group as a pH sensitive moiety.

The step of reacting the first macromonomer with the second macromonomer may comprise activating a terminal carboxylic acid group on either the first macromonomer or the second macromonomer. The activation may comprise reacting the terminal carboxyl group with an activating agent, e.g. N-hydroxysuccinimide to form an activated ester e.g. an N-hydroxysuccinimidyl ester. This reaction may be activated by DCC as described above. This reaction produces an activated macromonomer (an activated first macromonomer or an activated second macromonomer). The activated first or second macromonomer may be isolated (e.g. by filtration) and optionally dried before reacting with the second or first macromonomer respectively. The reaction of the first macromonomer with the second macromonomer may be conducted in a suitable solvent, e.g. DMSO or some other dipolar aprotic solvent. Thus the step of reacting the first macromonomer with the second macromonomer may comprise activating a terminal carboxyl group on the first macromonomer, e.g. by forming an N-hydroxysuccinimidyl ester of the first macromonomer, to form an activated first macromonomer, and reacting the activated first macromonomer with the second macromonomer. Alternatively it may comprise activating a terminal carboxyl group on the second macromonomer, e.g. by forming an N-hydroxysuccinimidyl ester of the second macromonomer, to form an activated second macromonomer, and reacting the activated second macromonomer with the first macromonomer.

In an embodiment, the process comprises:
copolymerising a temperature-sensitive monomer, a hydrophilic monomer and a substrate monomer to form a precursor macromonomer, whereby the substrate monomer comprises a functional group capable of reacting with a targeting compound or derivative thereof following said copolymerising in order to conjugate the targeting compound or derivative thereof to the precursor macromonomer,
conjugating the targeting compound to the precursor macromonomer to form a first macromonomer, and
reacting the first macromonomer with a second macromonomer, said second macromonomer comprising a plurality of hydrophobic monomeric units, and said hydrophobic block comprising at least one pH-sensitive moiety.

In another embodiment, the process comprises:
copolymerising a temperature-sensitive monomer, a hydrophilic monomer and a substrate monomer in the presence of a carboxyl functional chain transfer agent to form a carboxyl functional precursor macromonomer, whereby the substrate monomer comprises a functional group capable of reacting with a targeting compound or derivative thereof following said copolymerising in order to conjugate the targeting compound or derivative thereof to the precursor macromonomer,
conjugating the targeting compound to the precursor macromonomer to form a first macromonomer,
polymerising a hydrophobic monomer comprising at least one pH-sensitive moiety in the presence of an aminofunctional or hydroxyfunctional chain transfer agent to form an aminofunctional or hydroxyfunctional second macromonomer,
activating the first macromonomer to reaction with a terminal functional group (e.g. a hydroxyl or an amine group) on the second macromonomer, and
reacting the activated first macromonomer with the second macromonomer.

In another embodiment, the process comprises:
copolymerising a temperature-sensitive monomer, a hydrophilic monomer and a substrate monomer in the presence of a hydroxyfunctional or amino functional chain transfer agent to form a hydroxyfunctional or aminofunctional precursor macromonomer, whereby the substrate monomer comprises a functional group capable of reacting with a targeting compound or derivative thereof following said copolymerising in order to conjugate the targeting compound or derivative thereof to the precursor macromonomer,
conjugating the targeting compound to the precursor macromonomer to form a first macromonomer,
polymerising a hydrophobic monomer comprising at least one pH-sensitive moiety in the presence of a carboxyfunctional chain transfer agent to form a carboxyfunctional second macromonomer,
activating the second macromonomer to reaction with a terminal functional group (e.g. a hydroxyl or an amine group) on the first macromonomer, and
reacting the activated second macromonomer with the first macromonomer.

In another embodiment, the process comprises:
copolymerising a temperature-sensitive monomer, a hydrophilic monomer and a substrate monomer in the presence of a hydroxyfunctional or amino functional chain transfer agent to form a hydroxyfunctional or aminofunctional precursor macromonomer, whereby the substrate monomer comprises a functional group capable of reacting with a targeting compound or derivative thereof following said copolymerising in order to conjugate the targeting compound or derivative thereof to the precursor macromonomer,
conjugating the targeting compound to the precursor macromonomer to form a first macromonomer,
polymerising a hydrophobic monomer comprising at least one protected carboxyl group, e.g. a trimethylsilyl ester, in the presence of a carboxyfunctional chain transfer agent to form a carboxyfunctional second macromonomer,
activating the second macromonomer to reaction with a terminal functional group (e.g. a hydroxyl or an amine group) on the first macromonomer,
reacting the activated second macromonomer with the first macromonomer, and
deprotecting, e.g. hydrolysing, the protected carboxyl group to generate an unprotected carboxyl group.

In another embodiment the process comprises:
conjugating a targeting compound to a substrate monomer to form a targeting monomer, whereby the substrate monomer comprises a functional group capable of reacting with the targeting compound or derivative in order to conjugate the targeting compound or derivative thereof to the substrate monomer,
copolymerising a temperature-sensitive monomer, a hydrophilic monomer and the targeting monomer to form a first macromonomer, and
reacting the first macromonomer with a second macromonomer, said second macromonomer comprising a plurality of hydrophobic monomeric units, and said second macromonomer comprising at least one pH-sensitive moiety.

In another embodiment the process comprises:
copolymerising a temperature-sensitive monomer, a hydrophilic monomer and an aminofunctional monomer to form a precursor macromonomer,
conjugating a folic acid derivative to the precursor macromonomer to form a first macromonomer, and
reacting the first macromonomer with a second macromonomer, said second macromonomer being hydrophobic and comprising pH-sensitive moieties.

In another embodiment the process comprises:
copolymerising N-isopropylacrylamide, N,N-dimethylacrylamide and 2-aminoethylmethacrylate,
conjugating folic acid to the precursor macromonomer to form a first macromonomer, and
reacting the first macromonomer with a second macromonomer, said second macromonomer being a polymer of 10-undecenoic acid.

In another embodiment the process comprises:
copolymerising N-isopropylacrylamide, N,N-dimethylacrylamide and 2-aminoethylmethacrylate in the presence of a carboxyfunctional thiol to form a precursor macromonomer,
reacting an N-hydroxysuccinimide derivative of folic acid with the precursor macromonomer to form a first macromonomer,
activating the first macromonomer to reaction with an amine, to form an activated first macromonomer and
reacting the activated first macromonomer with a second macromonomer, said second macromonomer being a polymer of 10-undecenoic acid having a terminal amino group.

The invention also provides a block copolymer when made by the process of the second aspect.

In a third aspect of the invention there is provided a temperature and pH sensitive composition comprising:
a therapeutic agent, and
a block copolymer comprising at least a first block and a second block, wherein the first block comprises a plurality of temperature-sensitive monomeric units, a plurality of hydrophilic monomeric units and a plurality of targeting monomeric units, and the second block comprises a plurality of hydrophobic monomeric units, and said second block comprising at least one pH-sensitive moiety.

The block copolymer may be according to the first aspect, or may be made according to the second aspect. The therapeutic agent may be a drug, e.g. an anticancer drug, an anti-inflammatory drug or a drug to treat neurological disorders, or may comprise a mixture of two or more such drugs, or may be some other type of drug. The anticancer drug may be for example doxorubicin, anastrozole, exemestane, cyclophosphamide, epirubicin, toremifene, letrozole, trastuzumab, megestrol, nolvadex, paclitaxel, docetaxel, capecitabine, goserelin acetate, hydroxy urea, erythromycin, cyclosporin or cisplatin or a mixture of any two or more of these.

The composition may comprise, or be in the form of, micelles or nanoparticles. The micelles may be spherical, pseudospherical, substantially spherical, rounded, oblate spherical, ovoid or some other shape. The mean diameter of the micelles may be less than 250 nm, or less than about 200, 150, 100 or 50 nm, or between about 50 and about 250 nm, or between about 50 and 200, 50 and 150, 50 and 100, 100 and 250, 200 and 250, 100 and 200, 50 and 150 nm or 80 and 130, e.g. about 50, 60, 70, 80, 90, 100, 110, 120, 130, 140, 150, 200 or 250 nm, or may be larger than 250 nm. The copolymer may be arranged into at least one nanoparticle comprising a hydrophobic core and a hydrophilic shell. The therapeutic agent may be contained or located or distributed within the hydrophobic core. The shell may comprise targeting groups. At least some of the targeting groups may be on the outer surface of the nanoparticle.

In a fourth aspect of the invention there is provided a process for making a temperature and pH sensitive composition comprising combining a therapeutic agent with a solution of a block copolymer, said block copolymer comprising at least a first block and a second block, wherein the first block comprises a plurality of temperature-sensitive monomeric units, a plurality of hydrophilic monomeric units and a plurality of targeting monomeric units, and the second block comprises a plurality of hydrophobic monomeric units, and said second block comprising at least one pH-sensitive moiety. The solution of the block copolymer may be a micellar solution. The process may comprise making the composition in the form of micelles or nanoparticles, or may comprise converting the composition to micelles or nanoparticles. The micelles or nanoparticles may each comprise a hydrophobic core and a hydrophilic shell wherein the therapeutic agent is contained within said hydrophobic core.

The invention also provides a composition, nanoparticles or micelles, made by the process of the fourth aspect.

The solution of the block copolymer may be a solution in a suitable solvent. The suitable solvent may be a dipolar aprotic solvent. It may be water miscible. It may for example be dimethylacetamide, DMSO or some other suitable solvent. The therapeutic agent may be in solution when combined with the block copolymer solution. The therapeutic agent may be a neutralised therapeutic agent. The process may comprise neutralising the therapeutic agent. The combining may comprise one or more of mixing, swirling, sonicating, shaking, blending, vortexing, or some other form of agitating. The process may comprise one or more of:
dialysing the combined block copolymer solution and therapeutic agent in order to form micelles or nanoparticles comprising the therapeutic agent and the block copolymer and to remove therapeutic agent not incorporated into the micelles or nanoparticles and to remove block copolymer not incorporated into the micelles or nanoparticles, e.g. using a dialysis membrane with a molecular weight cutoff of between about 500 and about 40000, or between about 500 and 20000, 500 and 10000, 500 and 5000, 500 and 2000, 500 and 1500, 1500 and 3000, 1500 and 2000, 2000 and 3000, 1500 and 2500, 2000 and 10,000, 2000 and 40000, 5000 and 40000, 10000 and 40000, 20000 and 40000, 1000 and 20000, 1000 and 10000, 1000 and 5000 or above 40000, e.g. about 500, 1000, 1500, 1600, 1700, 1800, 1900, 2000, 2100, 2200, 2300, 2400, 2500, 2600, 2700, 2800, 2900, 3000, 4000, 5000, 6000, 7000, 8000, 9000, 10000, 15000, 20000, 25000, 30000, 35000 or 40000 or above 40000;

filtering the combined block copolymer solution and therapeutic agent through a filter e.g. a 0.45 micron, 0.3 micron, 0.2 micron or 0.1 micron pre size filter or membrane;

drying the filtrate, e.g. freeze drying.

In an embodiment, the process comprises:

combining a therapeutic agent with a solution of a block copolymer comprising at least a first block and a second block, wherein the first block comprises a plurality of temperature-sensitive monomeric units, a plurality of hydrophilic monomeric units and a plurality of targeting monomeric units, and the second block comprises a plurality of hydrophobic monomeric units, said second block comprising at least one pH-sensitive moiety;

dialysing the combined block copolymer solution and therapeutic agent using a dialysis membrane with a molecular weight cutoff of about 2000 in order to form micelles or nanoparticles comprising the therapeutic agent and the block copolymer;

filtering the dialysed combination of block copolymer solution and therapeutic agent through a 0.45 micron filter to isolate a filtrate (i.e. isolating the micelles or nanoparticles by filtration); and freeze-drying the filtrate (i.e. the micelles or nanoparticles).

In a fifth aspect of the invention there is provided a method of providing a therapeutic agent to a subject, e.g. an animal or human, comprising administering to said animal or human a temperature and pH-sensitive composition comprising:

a therapeutic agent, and a block copolymer comprising at least a first block and a second block, wherein the first block comprises a plurality of temperature-sensitive monomeric units, a plurality of hydrophilic monomeric units and a plurality of targeting monomeric units, and the second block comprises a plurality of hydrophobic monomeric units, and said second block comprising at least one pH-sensitive moiety;

wherein said copolymer is arranged into at least one nanoparticle comprising a hydrophobic core and a hydrophilic shell and wherein said therapeutic agent is contained, located or dispersed within said hydrophobic core.

The composition may be delivered orally, locally, intravenously, tropically, parenterally, through inhalation or through an ocular route. The therapeutic agent may comprise an anti-cancer drug. There may be targeting groups on the outer surface of the nanoparticle(s). The composition may be an anti-cancer composition. The targeting groups may be tumour targeting groups. The subject may be a human or a non-human animal. It may be a primate. It may be a domestic animal or it may be a non-domestic animal. It may be for example an ape, a monkey, a horse, a sheep, a cow, a bull, a goat, a pig, a dog, a cat, an elephant or some other type of animal.

There is also provided a block copolymer according to the first aspect, or a composition according to the third aspect, when used for providing a therapeutic agent to an animal or human.

In a sixth aspect of the invention there is provided a pharmaceutical composition comprising a composition according to the third aspect of the invention together and at least one pharmaceutically acceptable carrier and/or adjuvant. The carrier may for example comprise sterile water, water for injections, other suitable water, Ringers Solution, Hartmanns Solution, dextrose solution or saline solution. There is also provided the use of the pharmaceutical composition for the treatment of a condition in a patient, wherein the therapeutic agent is indicated for said treatment. The condition may be cancer, or a neurological disorder, or may be some other condition.

In a seventh aspect of the invention there is provided the use of a block copolymer according to the first aspect, or a composition according to the third aspect, for the manufacture of a medicament or pharmaceutical composition for the treatment of cancer or of a neurological disorder.

In an eighth aspect of the invention there is provided a precursor block copolymer comprising at least a first block and a second block, wherein the first block comprises a plurality of temperature sensitive monomeric units, a plurality of hydrophilic monomeric units and a plurality of substrate monomeric units, and the second block comprises a plurality of hydrophobic monomeric units, and said second block comprising at least one pH-sensitive moiety, wherein each substrate monomeric unit comprises a functional group capable of reacting with a targeting compound or derivative thereof in order to conjugate the targeting compound or derivative thereof to the precursor block copolymer.

The temperature-sensitive monomeric units, the hydrophilic monomeric units, the substrate monomeric units and the hydrophobic monomeric units may be as described earlier. The precursor block copolymer may be the same as the block copolymer of the first aspect with the exception that the targeting monomeric units are replaced by substrate monomeric units. Thus for example the molecular weight, numbers of monomers in blocks etc. may be as described for the block copolymer of the first aspect. Each of the temperature-sensitive monomeric units may be the same as the other temperature-sensitive monomeric units, or some may be the same and some may be different. Each of the hydrophilic monomeric units may be the same as the other hydrophilic monomeric units, or some may be the same and some may be different. Each of the substrate monomeric units may be the same as the other substrate monomeric units, or some may be the same and some may be different. Each of the hydrophobic monomeric units may be the same as the other hydrophobic monomeric units, or some may be the same and some may be different. The block copolymer may be capable of adopting a conformation in which the copolymer is in the form of a core-shell structure having a hydrophobic core and a hydrophilic shell wherein at least some of the substrate monomeric units are located in the hydrophilic shell. The block copolymer may have one of each block, or may have more than one of either the first block, the second block, or of both the first and second blocks. The block copolymer may be an AB block copolymer.

In a ninth aspect of the invention there is provided a process for making a precursor block copolymer comprising:

providing a precursor macromonomer, said precursor macromonomer comprising a plurality of temperature-sensitive monomeric units, a plurality of hydrophilic monomeric units and a plurality of substrate monomeric units, and reacting the precursor macromonomer with a second macromonomer, said second macromonomer comprising a plurality of hydrophobic monomeric units, and said second macromonomer comprising at least one pH-sensitive moiety.

The precursor macromonomer may be as described in the second aspect of the invention. The invention also provides a precursor block copolymer when made by the process of the ninth aspect.

In a tenth aspect of the invention there is provided a process for making a block copolymer comprising reacting a precursor block copolymer according to the eighth aspect of the invention, or a precursor block copolymer made by the process of the ninth aspect of the invention, with a targeting compound or derivative thereof in order to conjugate the targeting compound or derivative thereof to the precursor block copolymer. The block copolymer may be according to the first aspect of the invention.

BRIEF DESCRIPTION OF THE DRAWINGS

A preferred form of the present invention will now be described by way of example with reference to the accompanying drawings wherein.

DETAILED DESCRIPTION OF THE PREFERRED EMBODIMENTS

Figure 1:
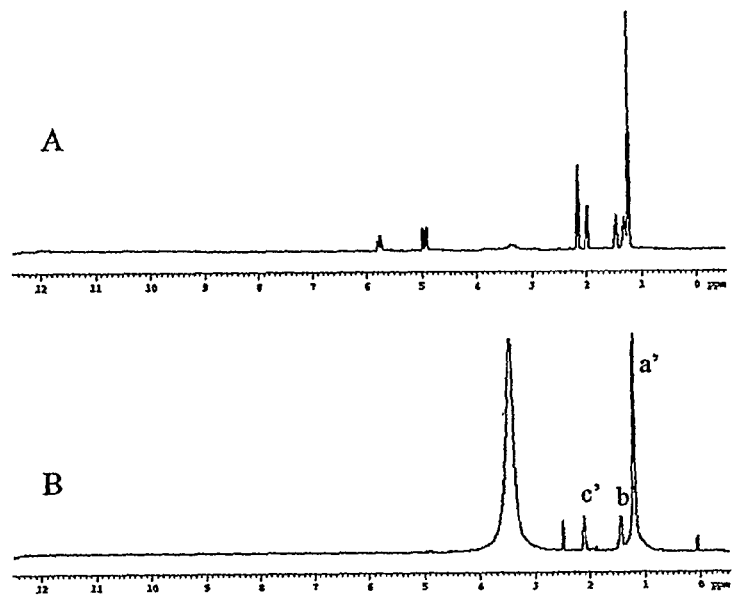
FIG. 1 shows $^1$H-NMR spectra of UA (A) and PUA (B) (d-DMSO as solvent)

In one embodiment the present specification discloses a block copolymer based on folate-conjugated poly(N-isopropylacrylamide-co-N,N-dimethylacrylamide-co-2-aminoethyl methacrylate)-b-poly(10-undecenoic acid)), which is pH- and temperature-sensitive. This polymer can self-assemble into core-shell nanoparticles. During the self-assembly process, one or more drugs may be encapsulated into the nanoparticles. The nanoparticles are stable under the normal physiological condition but deform in a low pH environment such as tumour tissues, endosomes or lysosomes. The targeting group (folate) directs the nanoparticles to tumour cells and the nanoparticles release the drug molecules into the cytosols (intracellular drug delivery). A biological signal (i.e. targeting group) is conjugated to the hydrophilic block of the polymer for targeting of cancer cells that over-express folate receptors.

More generally, there is disclosed herein a block copolymer of structure $(A_aB_bC_x)$-$D_y$, in which A is a temperature sensitive monomer unit, B is a hydrophilic monomer unit, C is a targeting monomer unit and D is a hydrophobic monomer unit, and a, b, x and y are greater than 1. The $A_aB_bC_x$ block may comprise a random copolymer block or a block copolymer block or an alternating copolymer block or some other type of copolymer block. The molecular weight of $(A_aB_bC_x)$-$D_y$ may be less than about 40,000 and the molecular weight of the $A_aB_bC_x$ may be less than about 40,000. The molecular weight of the $D_y$ block may be between about 200 and 2000, and may therefore considered to be an oligomeric block. The polydispersity of each block may, independently, be between about 1.1 and about 3. The number of temperature-sensitive monomeric units per molecule divided by the number of hydrophilic monomeric units per molecule may be between about 1 and about 100. The ratio of the sum of the number of temperature-sensitive monomeric units per molecule plus the number of hydrophilic monomeric units per molecule and the number of targeting monomeric units per molecule may be between about 500 and about 1. The ratio of the number of monomer units in the $A_aB_bC_x$ block and the number of monomer units in the $D_y$ block may be between about 2 and about 500. The block copolymer $(A_aB_bC_x)$-$D_y$ may be made by reacting a copolymer of structure $A_aB_bC_x$ with a polymer of structure, in particular a polymer of structure $A_aB_bC_x$-$G_1$ with a polymer of structure $D_y$-$G_2$, where $G_1$ and $G_2$ are groups which are capable of reacting to couple $A_aB_bC_x$-$G_1$ with $D_y$-$G_2$. Alternatively it may be made by reacting a block copolymer of structure $(A_aB_bS_x)$-$D_y$ with a targeting molecule, where S is a substrate monomer group capable of reacting with the targeting molecule to produce the targeting monomer unit C. Copolymer $A_aB_bC_x$ may be made by copolymerising monomers from which A, B and C are derived, or by reacting a copolymer of structure $A_aB_bS_x$ with the targeting molecule. Copolymer $A_aB_bS_x$ may be made by copolymerising the monomers from which A, B and S are derived.

The hydrophilic and hydrophobic blocks of the polymer are synthesized by radical copolymerization and the two blocks are then conjugated to form a block copolymer, which can self-assemble into core-shell nanostructures or nanoparticles (i.e. micelles). The micelles are capable of absorbing protons in the endosomes or lysosomes, breaking down the balance of proton concentration inside and outside of the endosomes or lysosomes and thus fusing with the endosome or lysosome membrane. In addition, the surface of the nanoparticles becomes hydrophobic in a low pH environment such as tumour sites, endosomes or lysosomes, thereby improving the attachment of the nanoparticles to the tumour sites or fusing with the endosome or lysosome membrane.

p(NIPAAm-co-DMAAm-co-AMA)-b-PUA is a block amphiphilic copolymer, which forms micelles with a more stable core for drug incorporation and smaller size with a more narrow distribution compared to the prior art. The polymer is capable of incorporating folate moieties in the hydrophilic block, leading to micelles having shells comprising folate molecules after self-assembly of the copolymer. These micelles are suited to target anticancer drugs to tumour cells that over-express folate receptor and release the drug molecules inside the cells to the cytosols, providing a better approach for cancer therapy. In the present work, the inventors have synthesized a multi-functional block copolymer folate-conjugated poly(N-isopropylacrylamide-co-N,N- dimethylacrylamide-co-2-aminoethyl methacrylate)-b-10-undecenoic acid (P(NIPAAm-co-DMAAm-co-AMA)-b-PUA). The monomer 2-aminoethyl methacrylate was employed to introduce amine groups for folate conjugation. The block copolymer is capable of self-assembly into micelles in aqueous solutions, each of said micelles having a shell containing folic acid molecules. These micelles also exhibited a pH-dependent LCST but more stable inner core and smaller size (<100 nm) with a narrower distribution when compared to P(NIPAAm-co-DMAAm-co-UA) micelles. Doxorubicin (DOX) was used as a model anticancer drug. DOX release was responsive to environmental pH changes. Cellular uptake and in vitro cytotoxicity of blank micelles, free DOX and DOX-loaded micelles against 4T1 mouse breast cancer cells were investigated and compared. A mouse breast cancer model induced by 4T1 cells was employed to study biodistribution of DOX and its blood concentration as a function of time. More DOX was accumulated in tumour tissue post-administration of DOX-loaded micelles when compared to free DOX. These multi-functional micelles may make a promising carrier to transport anticancer drugs specifically to tumour cells and release the drug molecules inside the cells to the cytosols.

In the present system, 10-undecenoic acid (UA) was polymerised to form PUA and a monomer with an amine group, 2-aminoethyl methacrylate (AMA), was copolymerised with N-isopropylacrylamide (NIPAAm) and N,N-dimethylacrylamide (DMAAm). The resulting poly(NIPAAm-co-DMAAm-co-AMA) was conjugated with folate, a targeting signal (tumour targeting compound) that can recognize cancer cells over-expressing folate receptors. Folate-conjugated P(NIPAAm-co-DMAAm-co-AMA) was further conjugated to PUA to form a multi-functional block copolymer, which was pH- and temperature-sensitive as well as sensitive to tumour cells. This amphiphilic block copolymer can self-assemble into micelles (core-shell nanoparticles), having a small size and narrow size distribution. In addition, the resulting micelles had a more stable core for drug incorporation when compared to P(NIPAAm-co-DMAAm-co-UA) micelles. These micelles would be able to target anticancer drugs to tumour cells that over-express folate receptor and release the drug molecules inside the cells to the cytosols, providing a better approach for cancer therapy.

Thus in one example, the present invention provides multifunctional micelles, for example in the form of core-shell nanoparticles, which may be self-assembled from folate-conjugated poly(N-isopropylacrylamide-co-N,N-dimethylacrylamide-co-2-aminoethylmethamlate)-b-poly(10-undecenoic acid) (P(NIPAAm-co-DMAAm-co-AMA)-b-PUA). The micelles may be used for targeted delivery of drugs, for example anticancer drugs. These micelles were demonstrated to have a better-defined core-shell structure, more stable core, smaller size with more narrow distribution when compared to the micelles made from the random copolymer poly(N-isopropylacrylamide-co-N,N-dimethylacrylamide-co-undecenoic acid) (P(NIPAAm-co-DMAAm-co-UA)) (disclosed in U.S. patent application Ser. No. 10/865,681). In a similar manner to P(NIPAAm-co-DMAAm-co-UA) micelles, P(NIPAAm-co-DMAAm-co-AMA)-b-PUA micelles also exhibited a pH-dependent LCST (lower critical solution temperature), which was higher than normal body temperature at pH 7.4 but lower than normal body temperature at pH 6.6 or below under a physiological condition. Therefore, the micelles were stable in PBS at pH 7.4 but deformed and precipitated, releasing the enclosed drug compounds at pH 6.6 or below.

In an example, a model anticancer drug, doxorubicin (DOX), was loaded into micelles of folate conjugated P(NIPAAm-co-DMAAm-co-AMA)-b-PUA by a membrane dialysis method. The DOX-loaded micelles were smaller than about 100 nm with a narrow size distribution. DOX release from the micelles was also pH-dependent, being much slower at pH 6.6 or below but faster at pH 7.4 at 37° C. Another feature of micelles according to the present invention is their ability to target anticancer drugs to tumour cells that over-express folate receptor, because folate molecules existed on the surfaces of the micelles. Thus, their cellular uptake by a model folate receptor-expressing cell line, 4T1 mouse breast cancer cells, was higher than for P(NIPAAm-co-DMAAm-co-UA) micelles without folate, leading to greater cytotoxicity. In vivo studies showed that DOX-loaded folate conjugated P(NIPAAm-co-DMAAm-co-AMA)-b-PUA micelles yielded higher DOX level in tumour tissues, lower level in the heart and prolonged blood circulation when compared to free DOX. The inventors hypothesise that the micelles stabilized DOX and reduced its uptake by the reticuloendothelial systems (RES) and the mononuclear phagocyte system (MPS). In addition, the reduction of DOX level in the heart may reduce the cardiotoxicity of DOX, a major side-effect of DOX. These multi-functional micelles may therefore be used as carriers for more efficient delivery of anticancer drugs.

Compared to the polymers disclosed in U.S. patent application Ser. No. 10/865,681, the block copolymer of the present invention provides micelles having a more stable core for drug incorporation and smaller size with a narrower distribution. Importantly, the polymer contains tumour targeting moieties e.g. folate moieties in the hydrophilic block, leading to micelles having shells with tumour targeting moieties after self-assembly. These micelles would be able to target anticancer drugs to tumour cells that over-express folate receptor and release the drug molecules inside the cells to the cytosols, providing a better approach for cancer therapy.

The present invention may be used for targeting drugs to tumour tissues with better efficacy than previous micelles. In addition, it may be used for in vitro and animal studies for drug discovery.

In the example described below, multi-functional block copolymer folate-conjugated poly(N-isopropylacrylamide-co-N,N-dimethylacrylamide-co-2-aminoethyl methacrylate)-b-poly(undecenoic acid) was successfully synthesized and utilized to fabricate micelles for targeted delivery of anticancer drugs. The micelles were spherical in nature, and the mean diameter of the blank and DOX-loaded micelles was less than 100 nm. The lower critical solution temperature (LCST) of the micelles was pH-dependent. Thus, particle size and dug release from micelles were also pH-dependent. The micelles were stable in PBS (pH 7.4) at 37° C., but deformed in an acidic environment, leading to fast drug release. DOX-loaded micelles with folate were taken up by folate receptor-expressing 4T1 cells via the folate receptor-mediated endocytosis process. Greater uptake was observed when compared to DOX-loaded micelles without folate, resulting in enhanced cytotoxicity. The results obtained from in vivo studies show that the DOX-loaded micelles self-assembled from this multi-functional polymer had a longer circulation time in the blood, and yielded a higher concentration in the tumours but lower concentration in the heart when compared to free DOX. The enhanced accumulation of DOX in the tumours using these micelles may provide a more efficient cancer therapy.

EXAMPLE

Materials and Methods

Materials

N-Isopropylacrylamide (NIPAAm, purchased from Sigma-Aldrich) was purified by re-crystallization from n-hexane. N,N-Dimethylacrylamide (DMAAm) and 10-undecenoic acid (98%, UA) were purchased from Sigma and vacuum distilled before use. Fetal serum albumin (FBS) was supplied from Invitrogen Corporation. Doxorubicin hydrochloride (DOX), pyrene, 3-mercaptopropionic acid (MPA), 2-aminoethyl methacrylate hydrochloride (90%), 2-aminoethanethiol (AET), N-hydroxysuccinimide (NHS), dicyclohexylcarbodiimide (DCC), 3-[4,5-dimethylthiazolyl-2]-2,5-diphenyl tetrazolium bromide (MTT), L-glutamine, acetonitrile (HPLC grade), anhydrous dichloromethane (DCM), anhydrous dimethyl sulfoxide (DMSO), N,N-dimethylacetamide (DMAc) and methanol (HPLC grade) were purchased from Sigma-Aldrich, and used as received. Ammonium persulphate (APS) was purchased from Bio-Rad Laboratories. Tetrahydrofuran (THF) and toluene were purchased from Merck, and dried over sodium. 4T1 cell lines were purchased from ATCC. All other chemicals were of analytical grade, and used as received.

Synthesis of folate-conjugated poly(N-isopropylacrylamide-co-N,N-dimethylacrylamide-co-2-aminoethyl methacrylate)-b-poly(10-udecenoic acid) (P(NIPAAm-co-DMAAm-co-AMA)-b-PUA)

Synthesis of P(NIPAAm-co-DMAAm-co-AMA)-COOH

Scheme 1
Synthesis of P(NIPAAm-co-DMAAm-co-AMA)-COOH.

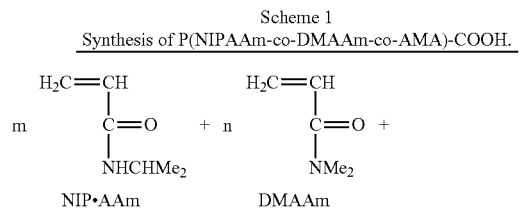

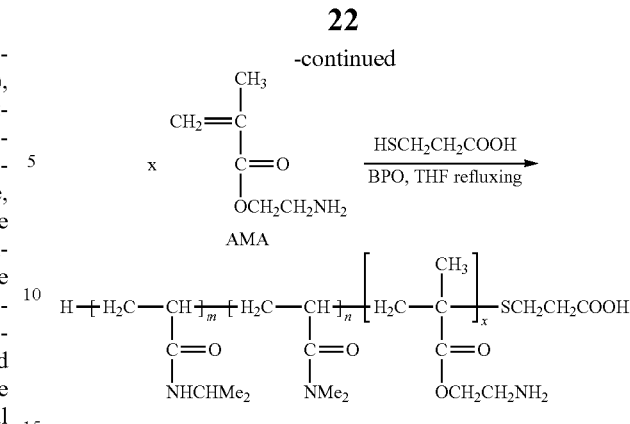

Carboxylic acid-terminated P(NIPAAm-co-DMAAm-co-AMA) precursor polymer was prepared by the radical copolymerization using benzoyl peroxide (BPO) as an initiator and 3-mercaptopropionic acid (MPA) as a chain transfer agent (Scheme 1). For instance, N-isopropylacrylamide (20.0 g, 176.9 mmol), N,N-dimethylacrylamide (3.50 g, 35.38 mmol), 2-aminoethyl methacrylate hydrochloride (90%) (158.4 mg, 0.86 mmol), MPA (269 mg, 2.54 mmol) and BPO (85.6 mg, 0.35 mmol) were dissolved in 30 mL of THF. The solution was degassed by bubbling with nitrogen for 20 minutes. The reaction mixture was refluxed for 8 hours under nitrogen at 85° C. Upon completion, the product was precipitated out by the addition of diethyl ether. The product was purified by re-precipitation three times from THF-diethyl ether using a slow liquid-liquid diffusion method, and then vacuum dried. It was further purified by dialyzing against de-ionized (DI) water for one week using a dialysis membrane with a molecular weight cut-off of 2000 (Spectra/Por 7, Spectrum Laboratories Inc.). The final product was harvested by freeze-drying.

Synthesis of folate-conjugated P(NIPAAm-co-DMAAm-co-AMA)-COOH

Scheme 2
Synthesis of folate-conjugated P(NIPAAm-co-DMAAm-co-AMA)-COOH.

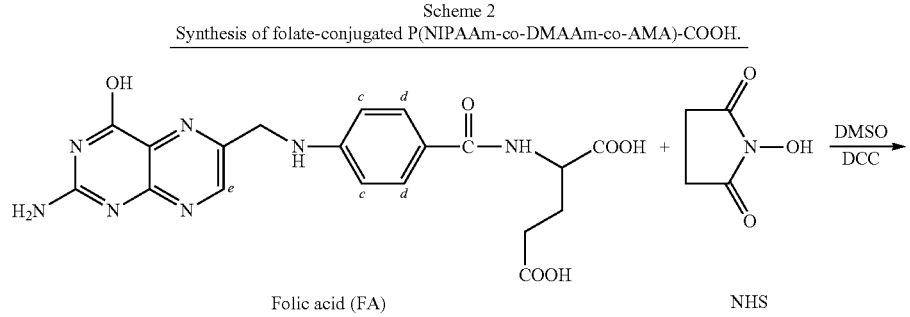

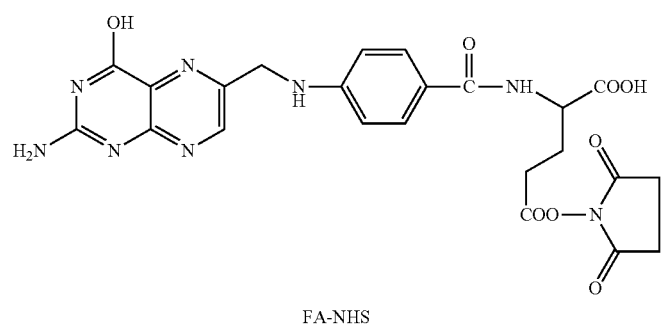

FA-NHS

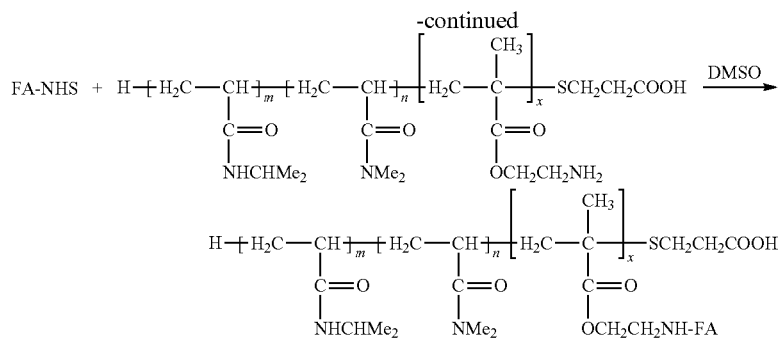

The carboxylic acid group of folic add (1.0 g, 2 mmol) dissolved in 20 mL of DMSO was pre-activated with DCC (0.495 g, 2.4 mmol) and NHS (0.463 g 4 mmol) at room temperature (Scheme 2). In the reaction, dicyclohexylurea was formed and removed by filtration. The vacuum-dried precursor polymer was added to the reaction solution. The reaction was kept at room temperature for 48 hours. The resulting solution was placed in a dialysis membrane with a molecular weight cut-off of 2000 and dialyzed against DI water for one week. The final product was harvested by freeze-drying.

Synthesis of PUA-NH$_2$

Scheme 3
Synthesis of PUA-NH$_2$.

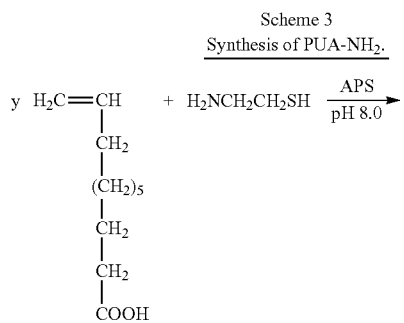

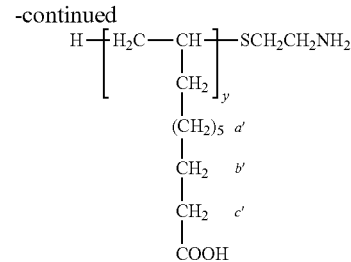

Amine-terminated poly(10-undecenoic acid) precursor polymer was prepared by the radical copolymerization using the redox agent ammonium persulfate (APS) as an initiator and 2-aminoethanethiol as a chain transfer agent. Briefly, 10-undecenoic acid (40.0 g, 217.0 mmol) was first converted into sodium salt by reacting with 100 mL of sodium hydroxide solution (0.1M), and the pH of the solution was adjusted to 8.0. The solution was bubbled with nitrogen overnight. Then, AET (2.0%-2.5% of the monomers in mole) and APS (4% of the monomers in weight) were added to the solution with stirring (Scheme 3). The reaction was kept at 70° C. for 48 hours. Upon completion, the crude product was precipitated by the addition of cold ethanol. The precipitates were re-dispersed three times in ethanol to remove un-reacted monomer. The product was dialyzed against DI water using a dialysis membrane with a molecular weight cut-off of 1,000 Da to remove the salt, and harvested by freeze-drying.

Conjugation of PUA-NH$_2$ to folate-conjugated P(NIPAAm-co-DMAAm-co-AMA)-COOH

Scheme 4
Synthesis of folate-conjugated P(NIPAAm-co-DMAAm-co-AMA)-b-PUA.

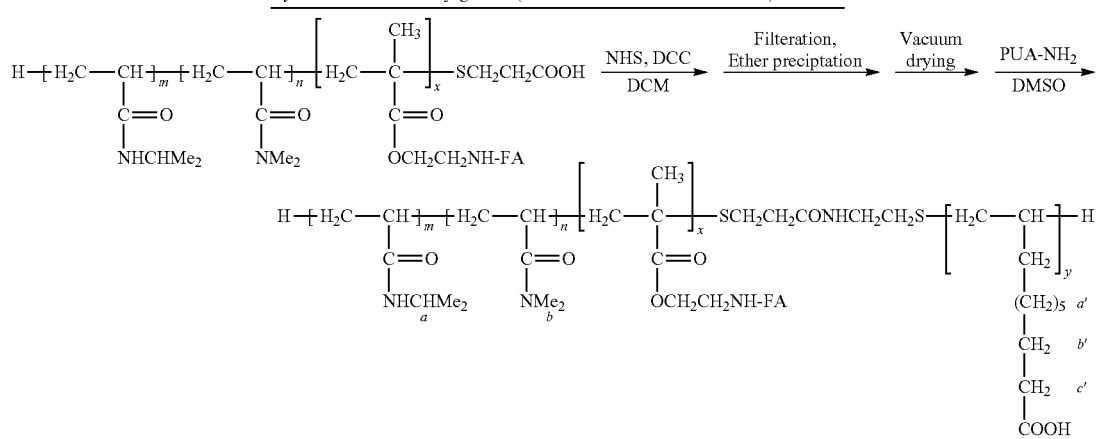

The carboxylic acid group of folate-conjugated P(NIPAAm-co-DMAAm-co-AMA)-COOH (1 mmol) was activated using DCC (1.2 mmol) and NHS (2 mmol) in DCM. Dicyclohexylurea was removed by filtration, and excess diethyl ether was added to precipitate the activated folate-conjugated P(NIPAAm-co-DMAAm-co-MAm)-COOH, which was further vacuum dried. The activated folate-conjugated P(NIPAAm-co-DMAAm-co-MAm)-COOH (1 gram) and an excess amount of PUA-$NH_2$ (3 grams) were dissolved in 30 mL of DMSO and stirred at room temperature for 48 h (Scheme 4). The un-reacted PUA-$NH_2$ was removed by dialysis against DMSO for one week using a membrane with a molecular weight cut-off of 3,500 Da, and DMSO was replenished daily. It was further dialyzed against DI water for another week. The final yellowish product was obtained by freeze-drying, and characterized by GPC, $^1$H-NMR, FTIR and titration.

Molecular Weight Analysis

Molecular weights of the polymers were determined by gel permeation chromatography (GPC) (Waters 2690, MA, USA) with a Differential Refractometer Detector (Waters 410, MA, USA). The mobile phase used was THF with a flow rate of 1 mL/min. Weight average molecular weights as well as polydispersity indices were calculated from a calibration curve using a series of polystyrene standards (Polymer Laboratories Inc., MA, USA, with molecular weight ranging from 1350 to 151,700).

Nuclear Magnetic Resonance (NMR) Analysis

The $^1$H-NMR spectra of the polymers were studied using a Bruker Avance 400 spectrometer (400 MHz), and chloroform-d ($CDCl_3$) was used as the solvent.

FT-IR Analysis

A Fourier transform infrared spectrophotometer (FT-IR, Perkin-Elmer Spectrum 2000) was employed to study the chemical structures of the polymers. The samples were pressed into potassium bromide pellets prior to FT-IR analysis.

Acid-Base Titration

Acid-base titration was performed to estimate carboxylic acid groups of the polymer. Briefly, 100 mg of polymer was dissolved in 10 mL of DI water and titrated with 0.01N NaOH using phenolphthalein as an indicator.

Optical Transmittance Measurements

Optical transmittance of aqueous polymer solution (5 mg/mL) at various temperatures was measured at 500 nm with a UV-VIS spectrometer (Jasco, V-570, Japan). Sample cells were thermostated with a temperature-controller. Heating rate was 0.1° C./min. The LCST values of polymer solutions were determined at the temperatures showing an optical transmittance of 50%.

Particle Size Analysis

The particle size of the micelles was measured using Zetasizer 3000 HAS (Malvem Instrument Ltd., Malvem, UK) equipped with a He—Ne laser beam at 658 nm (scattering angle: 90°. Each measurement was repeated 5 times. An average value was obtained from the five measurements. The size measurements were performed by multimodel analysis.

Transmission Electron Microscopy (TEM) Examinations

The morphologies of the blank and DOX-loaded micelles were analyzed by TEM (Philips CM300, Holland). Several drops of the freshly prepared micelles solution containing 0.01 (w/v) % phosphotungstic acid were placed on a copper grid coated with carbon film, and air-dried at room temperature. The observations were carried out with an electron kinetic energy of 300 k eV.

Critical Association Concentration

The critical association concentration (CAC) of the block polymer in DI water and PBS was estimated by fluorescence spectroscopy using pyrene as a probe. Fluorescence spectra were recorded by a LS50B luminescence spectrometer (Perkin Elmer, USA) at room temperature. Aliquots of pyrene solutions in acetone ($6.16 \times 10^{-5}$ M, 100 µL) were added to 15 mL volumetric flasks, and the acetone was allowed to evaporate. Then, 10 mL of polymer solutions with different concentrations ranging from 0.01 ppm to 500 ppm were added to the flasks. The final pyrene concentration is $6.16 \times 10^{-7}$ M. The solutions were equilibrated for 24 hours at room temperature (20° C.). The excitation spectra were recorded from 300 to 360 nm with an emission wavelength of 395 nm. Both excitation and emission bandwidths were set at 2.5 nm. The intensity ratios of 1335.5 to 1334.0 were plotted as a function of logarithm of polymer concentration. The CAC value was taken from the intersection of the tangent to the curve at the inflection with the horizontal tangent through the points at low concentrations.

Micelle Preparation

Blank and DOX-loaded micelles were prepared by a membrane dialysis method. For blank micelles, the polymer (20 mg) was dissolved in 4 mL of DMAc. The solution was then dialyzed against DI water at room temperature (20° C.) for 24 hours using a dialysis membrane with a molecular weight cut-off of 2,000 Da (Spectra/Por 7, Spectrum Laboratories Inc.). The water was replaced hourly for the first 3 hours. For DOX-loaded micelles, the polymer (20 mg) was dissolved in 2 mL of DMAc. DOX (10 mg) was neutralized with two moles excess triethylamine in 2 mL of DMAc. The DOX solution was added into the polymer solution and mixed by vortex for 5 minutes. The mixture was dialyzed against DI water at room temperature (20° C.) for 48 hours using a dialysis membrane with a molecular weight cut-off of 2,000 Da. After dialysis, the solution in the dialysis bag was collected, and filtered with 0.45 µm syringe filter and freeze-dried for two days. To determine DOX loading level, a known amount of DOX-loaded nanoparticles was dissolved in 1 mL of DMAc. The DOX concentration was estimated by using the UV-VIS spectrophotometer at 485 nm. The drug loading was calculated based on the standard curve obtained from DOX in DMAc. The yield of micelles was calculated as the weight ratio of micelles recovered to initial polymer and drug.

In Vitro Drug Release

The DOX-loaded micelles solutions prepared were diluted to 1 mg/mL. The diluted solutions (5 mL) were transferred to dialysis membrane tubes with a molecular weight cut-off of 10,000 Da (Spectra/Por 7, Spectrum Laboratories Inc.). The tubes were then immersed in a beaker containing 30 mL of PBS buffers (pH 7.4 and 6.6), which were shaken at a speed of 100 rev/min, and incubated at 37° C. At specific time intervals, 1 mL of solutions were withdrawn from the release medium and replaced with fresh PBS buffer. The DOX content in the samples was analyzed using the UV-VIS spectrophotometer at 485 nm.

Cellular Distribution of DOX

Free DOX (10 mg/L) and DOX-loaded micelles (DOX content: 10 mg/L) in RPMI 1640 medium (without folate) were incubated with 4T1 cells for 4 hours before examination. The cells on the cover glass were thoroughly washed three times with PBS and visualized by CLSM (Olympus FV300, Japan). DOX was excited at 532 nm with emission at 595 nm. The laser power was 10%. All the observations were conducted using the same resolution.

Cytotoxicity Test

4T1 mouse breast cancer cells were cultured in RPMI 1640 (without folate) supplemented with 10% FBS, 5% penicillin, 2 mM L-glutamine (Sigma), and incubated at 37° C., 5% $CO_2$. The cells were seeded onto 96-well plates at 10,000 cells per well, and incubated for one day. Free DOX, DOX-loaded micelles in RPM, 1640 were diluted with the growth medium to give final DOX concentrations of 0.01, 0.1, 1.0, 5.0, 10.0 and 20.0 mg/L. The blank polymer micelles in RPMI 1640 were diluted to 1, 10, 50.0, 100.0, 300.0 and 600.0 mg/L. The media in the wells were replaced with 100 μL of the pre-prepared samples. The plates were then returned to the incubator and maintained in 5% $CO_2$, at 37° C. for 48 hours.

Fresh growth media and 10 μL aliquots of MTT solution were used to replace the mixture in each well after 48 hours. The plates were then returned to the incubator and maintained in 5% $CO_2$, at 37° C., for a further 3 hours. The growth medium and excess MTT in each well were then removed. DMSO (150 μL) was then added to each well to dissolve the internalised purple formazan crystals. An aliquot of 100 μL was taken from each well and transferred to a fresh 96-well plate. Each sample was tested in eight replicates per plate. Three plates were used, making a total of 24 replicates per sample. The plates were then assayed at 550 nm and 690 nm. The absorbance readings of the formazan crystals were taken to be that at 550 nm subtracted by that at 690 nm. The results were expressed as a percentage of the absorbance of the blank control.

Animal Tests

Female balb/c (body weight: 19-21 g) were subcutaneously implanted with 4T1 cells ($10^7$ cells per animal). Tumours were allowed to grow for 2 weeks. Free DOX and DOX-loaded micelles were administered to the animals by tail vein injection at an equivalent DOX dose of 5 mg/kg. At 10 minutes, 30, minutes, 2 hours and 4 hours, blood samples were taken, and the animals were sacrificed. The liver, lung, heart, spleen, kidney and tumour were removed, and kept at −80° C. for future analysis. The organs were weighted and homogenized. DOX distributed in different organs was extracted using chloroform and isopropanol, and analyzed as described by H. S. Yoo, T. G. Park, *J. Control. Rel.* 2004, 100, 247. Homogenized tissue was added into an acidic hydrolysis buffer containing 2.0 M HCl solution at 80° C. for 10 minutes. The supernatant was collected, and 0.9 mL of the mixture of chloroform and isopropanol (3:1 in volume) was then added. After vortex-mixing, the organic layer was collected by centrifugation at 16,000 rpm for 15 minutes at room temperature. The solution was dried, and re-dissolved in a mobile phase and analyzed by high performance liquid chromatography (HPLC). The recovery rate was 70%, and corrected by an internal standard. The HPLC system consisted of a Waters 2690 separation module and Waters 2475 multi λ fluorescence detector. The mobile phase was composed of 0.01% trifluoroacetic acid aqueous solution and acetonitrile, and the percentage of aceonitrile was gradually increased from 5% to 45% in 40 minutes. The DOX peak was detected at an excitation wavelength of 480 nm and an emission wavelength of 580 nm.

Synthesis of folate-conjugated
P(NIPAAm-co-DMAAm-co-AMA)-b-PUA

The folate-conjugated copolymer was synthesized by multiple steps. Firstly, carboxylic acid-terminated P(NIPAAm-co-DMAAm-co-AMA) was prepared by the radical copolymerization of NIPAAm, DMAAm and AMA using benzoyl peroxide (BPO) as an initiator and 3-mercaptopropionic acid as a chain transfer agent. AMA monomer was introduced due to the presence of an amine group that could be employed for further conjugation of folic acid. The precursor polymer was obtained after purification by a liquid-liquid diffusion method (THF/$Et_2O$), followed by dialysis against DI water. The weight average molecular weight of this polymer was 6.8 kDa, having a polydispersity of 1.7 (Table 1).

TABLE 1

Properties of the copolymers.

| Samples | $M_w$ (kDa) | $M_n$ (kDa) | Poly-dispersity |
|---|---|---|---|
| Carboxylic acid-terminated P(NIPAAm-co-DMAAm-co-AMA) | 6.8 | 4.1 | 1.7 |
| Folate-conjugated P(NIPAAm-co-DMAAm-co-AMA)-COOH | 7.1 | 3.9 | 1.8 |
| Folate-conjugated P(NIPAAm-co-DMAAm-co-AMA)-b-PUA | 7.7 | 5.0 | 1.5 |

Figure 2:
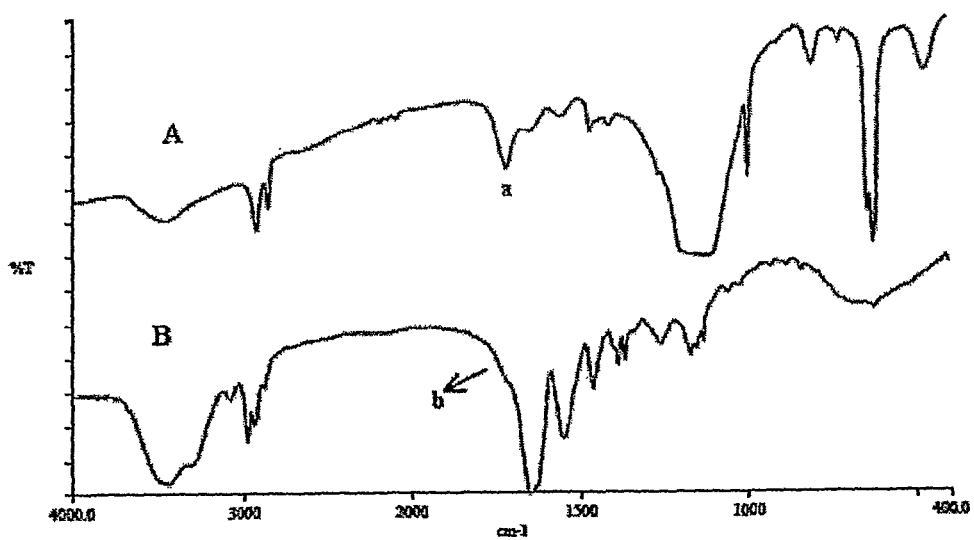
FIG. 2 shows FT-IR spectra of PUA-NH$_2$ (A) and folate-conjugated P(NIPAAm-co-DMAAm-co-AMA)-b-PUA (B) (where AMA is 2-aminoethyl methacrylate)
Figure 3:
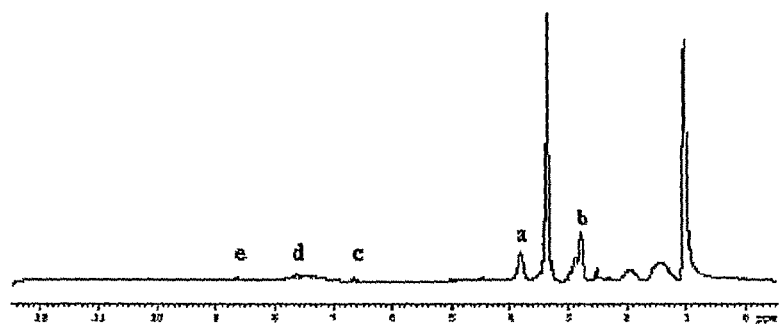
FIG. 3 is a $^1$H-NMR spectrum of folate-conjugated P(NIPAAm-co-DMAAm-co-AMA)-b-PUA (d-DMSO as solvent)

Subsequently, activated folic acid was conjugated to the amine group of P(NIPAAm-co-DMAAm-co-AMA)-COOH. Although folic acid has α- and γ-carboxylic acid groups, γ-carboxylic acid was primarily activated in the DCC/NHS reaction due to its higher reactivity. The resulting solution was centrifuged to discard the pellets, followed by dialysis against DI water. Folate-conjugated P(NIPAAm-co-DMAAm-co-AMA)-COOH was obtained after freeze-drying. The weight average molecular weight of this polymer was 7.1 kDa, having a polydispersity of 1.8. Thirdly, amine group-terminated PUA polymer was prepared by the radical copolymerization of UA using the redox agent ammonium persulfate (APS) as an initiator and 2-aminoethanethiol as a chain transfer agent. The success of the polymerization of UA monomer was evidenced by the absence of vinylic proton signals at δ 4.8-5.0 ($CH_2$=$CHCH_2$) and δ 5.7-5.9 ($CH_2$=$CHCH_2$) (FIG. 1A). The peaks at δ 1.3, 1.5 and 2.2 were assigned to $CH_2CH_2$ (Scheme 3, Signal a') $HOOCCH_2CH_2$ and $HOOCCH_2$ (Scheme 3, Signal b'), respectively (FIG. 1B). The lack of absorption at 3084 $cm^{-1}$ (=CH stretching) and 911 $cm^{-1}$ (HC=CH deformation) in the FT-IR spectrum of PUA-$NH_2$ further proved the successful polymerization of UA monomer (FIG. 2A). The spectrum of PUA-$NH_2$ also exhibited a carbonyl band ($v_{O-C=O}$, a) from the COOH group at 1712.3 $cm^{-1}$. Finally, the carboxylic acid group of folate-conjugated P(NIPAAm-co-DMAAm-co-MAm)-COOH was activated using DCC/NHS in DCM. The activated folate-conjugated poly(NIPAAm-co-DMAAm-co-MAm)-COOH was dissolved in DMSO, and reacted with an excess amount of PUA-$NH_2$. The NMR spectrum of the final product is shown in FIG. 3. The peak at δ 3.8 (Signal a) was contributed to the protons of —$NHCHMe_2$ groups in the NIPAAm moieties. The broad peak at δ 2.7-3.0 (Signal b) was from —$NMe_2$ groups in the DMAAm moieties. The weak peaks at δ 6.6 (Signal c), δ 7.7 (Signal d) and δ 8.7 (Signal e) were from folic acid moieties. The molar ratio of NIPAAm to DMAAm to folate was 3.7:1:0.026, which was obtained from the integration values of signals a, b and c (FIG. 3). The FTIR spectrum exhibits two strong absorptions at 1647.1 $cm^{-1}$ ($v_{HN-C=O}$) and 1547.8 $cm^{-1}$ ($v_{C-N}$) is coming from the P(NIPAAm-co-DMAAm-co-AMA) block. Another weak absorption at 1720 $cm^{-1}$ ($v_{O-C=O}$, b) was from the PUA-$NH_2$ block and folate moieties (FIG. 2B). The weight average molecular weight of the final product was 7.7 kDa with a polydispersity of 1.5 (Table 1). The increase of Mw indicates that PUA-$NH_2$ was successfully conjugated to folate-conjugated P(NIPAAm-co-DMAAm-co-AMA)-COOH. The COOH content was estimated by titration to be 18.4 mg per gram of polymer.

LCST of Micelles and Effect of pH

Figure 4:
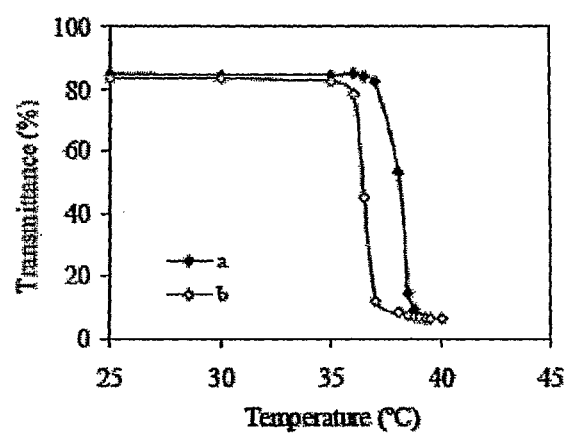
FIG. 4 is a plot of transmittance of micelles in PBS (phosphate buffer solution) as a function of temperature at varying pH at 500 nm: (a) pH 7.4; (b) pH 6.6.

PNIPAAm exhibits an LCST of 32° C. in water. The LCST can be modulated to be slightly higher than the normal body temperature (37° C.) in the physiological environment by introducing a hydrophilic monomer (e.g. DMAAm). The LCST of the micelles self-assembled from folate-conjugated P(NIPAAm-co-DMAAm-co-AMA)-b-PUA was measured in phosphate-buffered saline (PBS) solutions of different pH. As shown in FIG. 4, it was pH-dependent. For instance, at pH 7.4, the LCST was 38.0° C., well above the normal body temperature. However, at pH 6.6, it reduced to 36.2° C., lower than 37° C. With the increase of pH of the external environment, the carboxylic acid groups in the 10-undecenoic acid segment and folate were more easily de-protonated and thus increased the hydrophilicity of the polymer. This would lead to an increase in the LCST of the polymer, and hence, that of the nanoparticles. The higher the pH, the greater was the LCST. Since the LCST of the micelles was higher than the normal body temperature in the physiological environment (PBS, pH 7.4) but lower than the normal body temperature in acidic environments (e.g. lower than pH 6.6), these micelles can be used for intracellular drug delivery. In the endosomes and lysosomes where pH ranges from 4.0 to 6.5, the core-shell structure of the micelles may deform, releasing the enclosed drug molecules. On the other hand, the micelles adsorbed protons and the shell of the micelles became hydrophobic due to the decrease in the LCST in these environments, causing an increase in endosomal/lysosomal membrane permeability and thus promoting the transportation of the enclosed dug molecules into the cytoplasm.

CAC Determination

Figure 5:
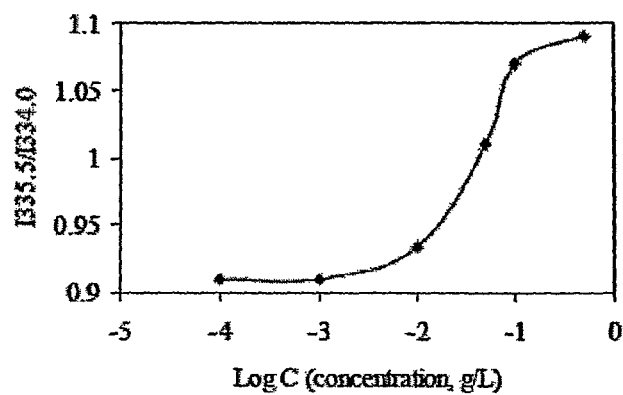
FIG. 5 is a plot of intensity ratio of I335.5/I334.0 as a function of logarithm of polymer concentration (log C) in deionised water.

The CAC of the polymer was analyzed by fluorescence spectroscopy using pyrene as a probe. The excitation spectra of pyrene are illustrated in FIG. 5A. As polymer concentration increased, the fluorescence intensity increased and the third peak shifted from 334.0 nm to 335.5 nm. The red to shift of the third peak indicates that pyrene molecules were transferred to the less polar domains of the core of the micelles. FIG. 5B shows the change in the ratio of I334.0 to I335.5 against polymer concentrations in DI water. The CAC value was determined to be 17.8 mg/L. It was noticed that the change in $I_3/I_1$ obtained from the emission spectra of pyrene after the formation of the micelles self-assembled from the block copolymer was much greater when compared to micelles made from the random copolymer. P(NIPAAm-co-DMAAm-co-UA), suggesting the formation of a more hydrophobic core possibly attributed to the presence of a greater number of UA units and better defined core-shell structure.

pH Effect on Structural Change of Micelles

Figure 6:
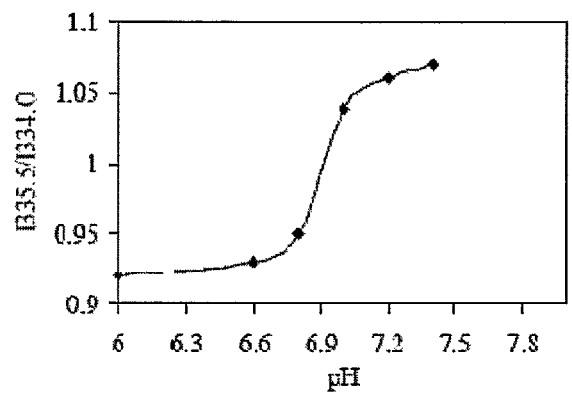
FIG. 6 is a plot of intensity ratio of I335.5/I334.0 as a function of pH for the polymer in different buffer.

To study the effect of pH on the structural change of the micelles, the change in the intensity ratio (I335.5/I334.0) of pyrene was investigated at 37° C. in the presence of the polymer dissolved in PBS of different pH but with an identical ionic strength of 154 mM. As shown in FIG. 6, for the micelles at pH 7.4 and pH 7.2, the ratio was high, indicating that pyrene molecules were in a low polar microenvironment. However, it dropped rapidly as the pH decreased from 7.0 to 6.8, suggesting that pyrene molecules were exposed to a more polar environment (i.e. the aqueous medium). As discussed in the previous section, carboxylic acid groups in the micelles protonated easily at pH 6.8 or below, leading to an LCST lower than 37° C. and thus the deformation of the core-shell structure of the micelles. This allowed pyrene molecules to be exposed to the aqueous medium. This finding further proved that the core-shell structure was sensitive to the external pH change.

Size, Size Distribution and Morphology of Micelles

TABLE 2

Properties of the blank and DOX-loaded micelles

| Samples | Effective diameter (nm) | Polydispersity |
|---|---|---|
| Blank micelles | 92.8 ± 0.1 | 0.27 ± 0.01 |
| DOX-loaded micelles | 98.5 ± 2.1 | 0.28 ± 0.01 |

Figure 7:
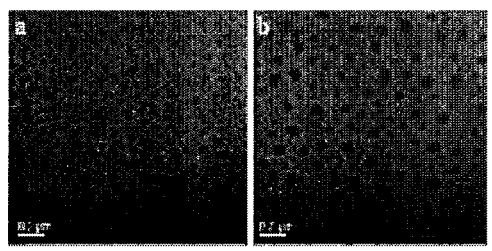
FIG. 7 shows transmission electron microscopy (TEM) images of the blank micelles (a) and the DOX (doxorubicin)-loaded micelles (b)

Table 2 lists the size and size distribution of the blank and DOX-loaded micelles fabricated in DI water. It was found that the micelles had a relatively narrow size distribution. The average effective diameter of the blank and DOX-loaded micelles was 92.8 nm and 98.5 nm, respectively. SEM images indicate that the blank and DOX-loaded micelles are spherical in nature (FIG. 7). The particle size observed from the TEM images was in good agreement with that measured by dynamic light scattering. Physical stability of the micelles is another important aspect to be considered for clinical applications because the aggregation of micelles may cause blood vessel occlusion and make them more susceptible to clearance by the reticuloendothelial systems (RES). The particle size did not change much in PBS (pH 7.4) over one week at room temperature, ranging from 87.0 nm to 97.0 nm, suggesting that the micelles were stable. On the other hand, the particle size did not vary significantly after five times dilution (87.0 nm vs. 92.1 nm). This is crucial since the dissociation of micelles after administration may lead to rapid release of the enclosed drug, resulting in side effects in vivo. Furthermore, it was observed that the size of the blank micelles kept constant after being challenged by 10% bovine serum albumin (BSA) in PBS (pH 7.4), indicating that the interactions between the micelles and BSA were well prevented by the hydrophilic shell and negative charges caused by the de-protonation of carboxylic acid groups in the folic acid molecules at pH 7.4. It is expected that the micelles may have good physical stability in vivo. The size of the micelles in PBS at 37° C. was pH-dependent, being 117.2 nm and 612.6 nm in pH 7.4 and pH 6.6 respectively. The increase in the particle size was due to the aggregation of the micelles in pH 6.6. In addition, the particle size was also temperature-dependent. For instance, in PBS (pH 7.4), the particle size of the micelles increased to 740.0 nm when the temperature was raised to 40° C. because of the aggregation of the micelles above the LCST. These findings indicate that the micelles were both pH- and temperature-sensitive. In particular, the change in the particle as size was reversible.

In Vitro Drug Release

Figure 8:
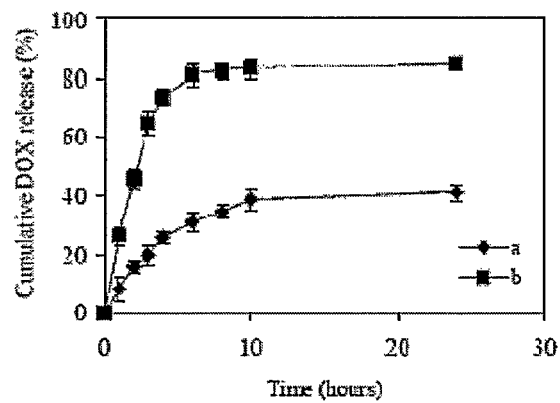
FIG. 8 shows release profiles of DOX from the micelles incubated at 37° C. (a) pH 7.4; (b) pH 6.6.

The actual loading level of DOX in the micelles was about 2.5% in weight. FIG. 8 shows in vitro release profiles of DOX from the micelles at 37° C. under a simulated physiological condition (PBS, pH 7.4) and in an acidic environment (pH 6.6). DOX release was much faster at pH 6.6 when compared to that at pH 7.4, having approximately 85% and 40% of the drug released, respectively, within 24 hours. At pH 6.6, the LCST of the micelles decreased to 36.2° C., leading to the hydrophobic shells of the micelles. The loss of hydrophilicity/hydrophobicity balance (HLB) of the micelles resulted in the eventual deformation of the core-shell structure, releasing the enclosed drug molecules.

Cellular Uptake and Cytotoxicity of DOX-Loaded Micelles

Figure 9:
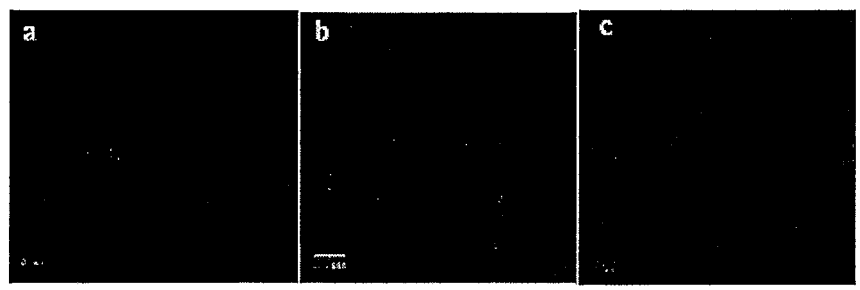
FIG. 9 shows confocal microscopic images of: (a) 4T1 cells incubated with free DOX; (b) DOX-loaded micelles made from P(NIPAAm-co-DMAAm-co-UA); and (c) folate-conjugated P(NIPAAm-co-DMAAm-co-AMA)-b-PUA (DOX concentration=10 mg/L)

Cellular uptake of free DOX and DOX-loaded micelles by 4T1 cells was examined by confocal microscopy. As shown in FIG. 9, when free DOX was incubated with 4T1 cells, doxorubicin molecules were transported into the cells through a passive diffusion pathway, and only accumulated in the nucleus. However, strong fluorescence was observed in the cytoplasm as well as the nucleus when the cells were incubated with the DOX-loaded micelles. The strong signals appeared in the nucleus were attributed to the doxorubicin molecules released from the micelles. This finding indicates that the DOX-loaded micelles were internalized by the cells through an endocytosis process, and then escaped from the endosome and/or the lysosome to enter the cytoplasm. In addition, the cellular uptake of DOX-loaded micelles made from folate-conjugated P(NIPAAm-co-DMAAm-co-AMA)-b-UA was higher than that of DOX-loaded P(NIPAAm-co-DMAAm-co-UA) micelles without folate probably because folate receptor-mediated endocytosis is more specific.

Figure 10:
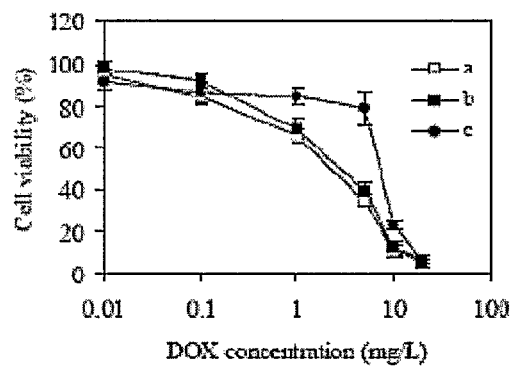
FIG. 10 is a graph showing viability of 4T1 cells after incubation with DOX, DOX-loaded P(NIPAAm-co-DMAAm-co-UA) and folate-conjugated P(NIPAAm-co-DMAAm-co-AMA)-b-PUA micelles at 37° C. for 48 hours.

Cell cytotoxicity of free DOX and DOX-loaded micelles against 4T1 cells was investigated. The IC50 value of DOX, a concentration at which 50% cells are killed, was 3.0, 3.8 and 7.6 mg/L for free DOX, DOX-loaded micelles with folate and without folate respectively (FIG. 10). The cytotoxicity of DOX-loaded micelles with folate against 4T1 cells was much greater than that of DOX-loaded micelles without folate because of higher cellular uptake. It should be mentioned that no cytotoxcicity was observed for blank micelles at a concentration of up to 500 mg/L.

In Vivo Tests

Figure 11:
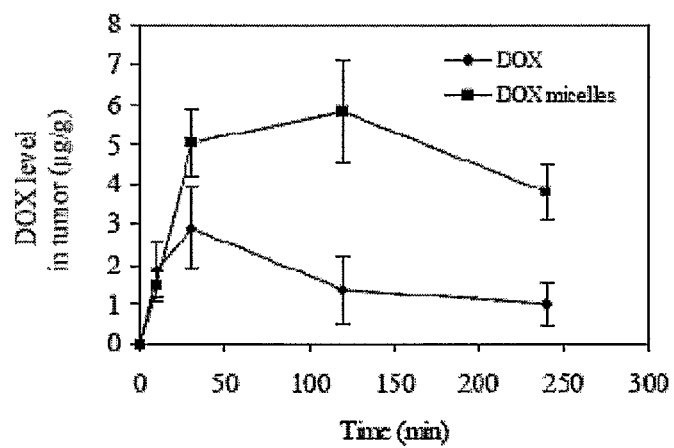
FIG. 11 is a graph showing DOX concentration in a tumour for the formulations of free DOX and DOX-loaded micelles.
Figure 12:
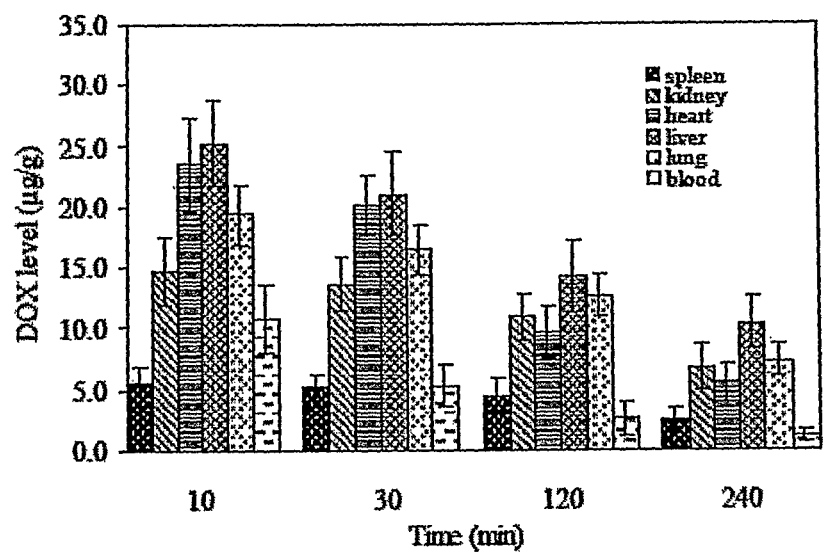
FIG. 12 is a graph showing biodistribution profiles of free DOX.
Figure 13:
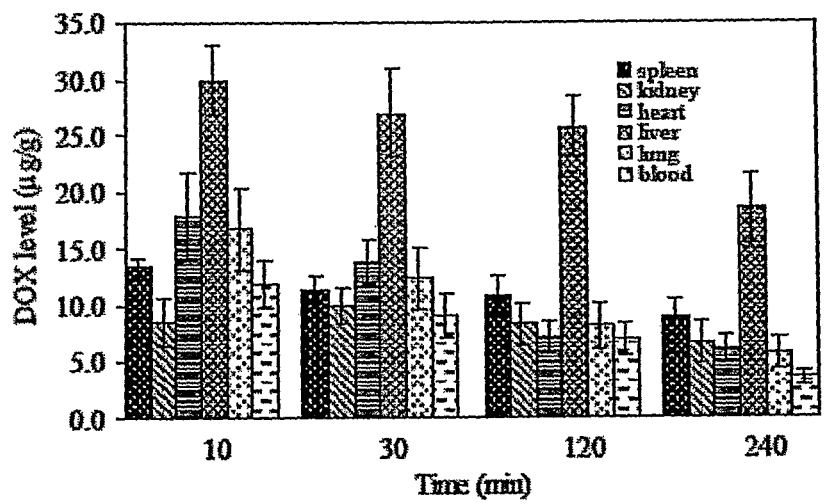
FIG. 13 is a graph showing biodistribution profiles of DOX-loaded micelles.

Animal studies were carried out to study the biodistribution of free DOX and DOX-loaded micelles using mice bearing subcutaneous 4T1 breast tumours. FIG. 11 shows DOX levels in tumour tissue as a function of time after the administration of free DOX and DOX-loaded micelles. For free DOX, the maximum DOX level was reached at 30 minutes, being 2.9 µg/g but the DOX level decreased rapidly, only 1.0 µg/g at 240 minutes. In contrast, DOX maintained a higher level up to 240 minutes in the formulation of micelles. This may be due to the EPR effect and enhanced cellular uptake of DOX-loaded micelles based on the folate receptor-mediated endocytosis process. In addition, DOX levels in the blood were also analyzed. As shown in FIGS. 12 and 13, for free DOX, DOX level in the blood decreased much more rapidly when compared to DOX-loaded micelles. Clearly, DOX-loaded micelles exhibited a longer circulation time, which is consistent with the results reported by J. W. Cowens, P. J. Creaven, W. R. Greco, D. E. Brenner, Y. Tung, M. Ostro, F. Pilkiewicz, R. Ginsberg, N. Petrelli, Cancer Research 1993, 53, 2796. The $t_{1/2}$ of free DOX and DOX-loaded micelles in the blood was about 30 minutes and 140 minutes respectively. This prolonged circulation may be due to the fact that the micelles reduced the uptake of DOX by the RES and the mononuclear phagocyte system. FIGS. 12 and 13 also display DOX levels in various organs such as the spleen, kidney, heart, liver and lung. Free DOX had a wide distribution, accumulating uniformly in the heart, lung and liver. However, in the formulation of micelles, DOX was preferentially accumulated in the organs rich in the RES, such as the liver and spleen. A significant reduction in DOX level was found in heart, indicating that the micelles might be able to reduce the cardiotoxicity of DOX, a major side-effect of DOX.

The above examples are provided to illustrate the invention, but not to limit its scope. Other variants of the invention will be readily apparent to one of ordinary skill in the art and are encompassed by the appended claims. All publications, patents, and patent applications cited herein are hereby incorporated by reference for all purposes.

The invention claimed is:

1. A block copolymer comprising at least a first block and a second block, wherein the first block comprises a plurality of temperature-sensitive monomeric units, a plurality of hydrophilic monomeric units and a plurality of targeting monomeric units, and the second block comprises a plurality of hydrophobic monomeric units, said second block comprising at least one pH-sensitive moiety and having a number average molecular weight of from about 200 to about 2000.

2. The block copolymer of claim 1 wherein the targeting monomeric units are tumor targeting monomeric units.

3. The block copolymer of claim 1 wherein each of the hydrophobic monomeric units comprises at least one pH-sensitive moiety.

4. The block copolymer of claim 1 wherein the hydrophobic monomeric units are derived from a polymerisable unsaturated fatty acid.

5. The block copolymer of claim 1 wherein the temperature sensitive monomeric units are derived from N-acryloylpiperidine, N-acryloylpyrrolidone, N-hydroxypropyl acrylate, N-t-butylacrylamide, N-piperidylmethacrylamide, N, N-diethylacrylamide, N-isopropylacryiamide, N-methacryloylpiperidine, N-methacryloylpyrrolidone, N-hydroxypropyl methacrylate, hydroxyethylcellulose, N-t-butylmethacrylamide, N,N-diethylmethacrylamide or N-isopropylmethacrylamide.

6. The block copolymer of wherein the hydrophilic monomeric units are derived from a species selected from the group consisting of acrylic acid, acrylamide (AAm), acrylate, pyrrolidone, ethylene glycol, 2-aminoethylmethacrylate, N,N'-dimethylacrylamide (DMAAm), and N-(hydroxymethyl) acrylamide and substituted, derivatives thereof.

7. The block copolymer of claim 1 wherein the targeting monomeric units comprise folate, galactose, a peptide, an antibody or an antibody fragment.

8. The block copolymer of claim 1 wherein the lower critical solution temperature (LCST) of the copolymer is lower than about 37° C. at a pH of about 6.6 to about 1.

9. The block copolymer of claim 1 wherein the lower critical solution temperature of the copolymer is higher than about 37° C. at normal physiological pH.

10. The block copolymer of claim 1 wherein the temperature sensitive monomeric units are derived from N-isopropylacrylamide, the hydrophilic monomeric units are derived from N,N-dimethylacrylamide, the targeting monomeric units are folate conjugated monomeric, units derived from 2-aminoethylmethacrylate and the hydrophobic monomeric units are derived from 10-undecenoic acid.

11. A process for making a block copolymer comprising:
providing a first macromonomer, said first macromonomer comprising a plurality of temperature-sensitive monomeric units, a plurality of hydrophilic monomeric units and a plurality of targeting monomeric units, and
reacting the first macromonomer with a second macromonomer, said second macromonomer comprising a plurality of hydrophobic monomeric units, and said second macromonomer comprising at least one pH-sensitive moiety and having a number average molecular weight of between about 200 and about 2000.

12. The process of claim 11 wherein the step of providing the first macromonomer comprises reacting a precursor macromonomer with a targeting compound or a derivative thereof.

13. The process of claim 12 comprising copolymerising a temperature-sensitive monomer, a hydrophilic monomer and a substrate monomer to form the precursor macromonomer, whereby the substrate monomer comprises a functional group capable of reacting with the targeting compound or a derivative thereof following said copolymerising in order to conjugate the targeting compound or derivative thereof to the precursor macromonomer.

14. The process of claim 11 wherein the step of providing the first macromonomer comprises copolymerising a temperature-sensitive monomer, a hydrophilic monomer and a targeting monomer derived from conjugating a targeting molecule with a substrate monomer.

15. The process of claim 13 wherein said copolymerising is conducted in the presence of a mercaptan chain transfer agent which is carboxyfunctional, aminofunctional or hydroxyfunctional or which comprises a functional group capable of being converted into a carboxylic acid group, an amino group or a hydroxyl, group.

16. The process of claim 14 wherein said copolymerising is conducted in the presence of a mercaptan chain transfer agent which is carboxyfunctional, aminofunctional or hydroxyfunctional or which comprises a functional group capable of being converted into a carboxylic acid group, an amino group or a hydroxyl group.

17. The process of claim 11 comprising the step of making the second macromonomer by polymerising a polymerisable hydrophobic monomer comprising at least one pH-sensitive moiety or comprising a functional group which can be converted into a pH-sensitive moiety.

18. The process of claim 17 wherein said polymerising is conducted in the presence of a chain transfer agent, said chain transfer agent being a thiol comprising a functional group capable of reacting with a terminal group of the first macromonomer.

19. A temperature and pH sensitive composition comprising: a therapeutic agent, and a block copolymer comprising at least a first block and a second block, wherein the first block comprises a plurality of temperature-sensitive monomeric units, a plurality of hydrophilic monomeric units and a plurality of targeting monomeric units, and the second block comprises a plurality of hydrophobic monomeric units, said second block comprising at least one pH-sensitive moiety and having a number average molecular weight between about 200 and about 2000.

20. A method of providing a therapeutic agent to an animal or human, comprising administering to said animal or human a temperature and pH-sensitive composition comprising:

a therapeutic agent, and a block copolymer, said block copolymer comprising at least a first block and a second block, wherein the first block comprises a plurality of temperature-sensitive monomeric units, a plurality of hydrophilic monomeric units and a plurality of targeting monomeric units, and the second block comprises a plurality of hydrophobic monomeric units, said second block comprising at least one pH-sensitive moiety;

wherein said copolymer is arranged into at least one nanoparticle, comprising a hydrophobic core and a hydrophilic shell and wherein said therapeutic agent is contained within said hydrophobic core and having a number average molecular weight of between about 200 and about 2000.

* * * * *